United States Patent
Harashima et al.

(10) Patent No.: US 11,814,640 B2
(45) Date of Patent: *Nov. 14, 2023

(54) RECOMBINANT EXPRESSION VECTOR AND LIPID MEMBRANE STRUCTURE HAVING SAID VECTOR ENCAPSULATED THEREIN

(71) Applicant: NATIONAL UNIVERSITY CORPORATION HOKKAIDO UNIVERSITY, Sapporo (JP)

(72) Inventors: Hideyoshi Harashima, Sapporo (JP); Yuma Yamada, Sapporo (JP); Takuya Ishikawa, Sapporo (JP); Hidetaka Akita, Sapporo (JP)

(73) Assignee: LUCA Science Inc., Tokyo (JP)

( * ) Notice: Subject to any disclaimer, the term of this patent is extended or adjusted under 35 U.S.C. 154(b) by 719 days.

This patent is subject to a terminal disclaimer.

(21) Appl. No.: 15/778,705

(22) PCT Filed: Nov. 28, 2016

(86) PCT No.: PCT/JP2016/085098
§ 371 (c)(1),
(2) Date: May 24, 2018

(87) PCT Pub. No.: WO2017/090763
PCT Pub. Date: Jun. 1, 2017

(65) Prior Publication Data
US 2018/0362999 A1 Dec. 20, 2018

(30) Foreign Application Priority Data
Nov. 26, 2015 (JP) ................................. 2015-230498

(51) Int. Cl.
| | | |
|---|---|---|
| C12N 15/85 | (2006.01) | |
| C12N 15/09 | (2006.01) | |
| A61K 9/127 | (2006.01) | |
| A61K 48/00 | (2006.01) | |
| C12N 15/113 | (2010.01) | |
| C12N 15/62 | (2006.01) | |
| C12N 15/67 | (2006.01) | |
| C12N 15/88 | (2006.01) | |

(52) U.S. Cl.
CPC ........ *C12N 15/8509* (2013.01); *A61K 9/1271* (2013.01); *A61K 48/0033* (2013.01); *A61K 48/0058* (2013.01); *A61K 48/0075* (2013.01); *C12N 15/09* (2013.01); *C12N 15/113* (2013.01); *C12N 15/62* (2013.01); *C12N 15/67* (2013.01); *C12N 15/88* (2013.01); *C07K 2319/07* (2013.01)

(58) Field of Classification Search
None
See application file for complete search history.

(56) References Cited

U.S. PATENT DOCUMENTS

| | | |
|---|---|---|
| 8,981,044 B2 | 3/2015 | Harashima et al. |
| 2007/0196334 A1 | 8/2007 | Khan |
| 2010/0111911 A1 | 5/2010 | Guy et al. |
| 2013/0122054 A1 | 5/2013 | Harashima et al. |
| 2013/0274314 A1 | 10/2013 | Palladino et al. |
| 2014/0196172 A1 | 7/2014 | Eudes et al. |
| 2015/0065556 A1* | 3/2015 | Birsoy ................ C12N 15/113 514/44 A |
| 2015/0225740 A1 | 8/2015 | Corral-Debrinski et al. |
| 2015/0315608 A1 | 11/2015 | Seibel |

FOREIGN PATENT DOCUMENTS

| | | |
|---|---|---|
| JP | 2007-524392 | 8/2007 |
| JP | 5067733 B2 | 11/2012 |
| JP | 2014-522662 | 9/2014 |
| WO | 2006095837 A1 | 9/2006 |
| WO | WO 2006/095837 | 9/2006 |

(Continued)

OTHER PUBLICATIONS

Yu et al. Mutant NADH dehydrogenase subunit 4 gene delivery to mitochondria by target sequence-modified adenovirus-associated virus induces visual loss and optic atrophy in mice. Molecular Vision. Jun. 20, 2012. vol. 18, pp. 1668-1683. (Year: 2012).*
Sequence Alignment of SEQ ID No. 13 with SEQ ID No. 1 of U.S. Pat. No. 8,981,044. Search conducted on Apr. 12, 2021, 1 page. (Year: 2021).*
Inagaki et al., "Inhibition of Mitochondrial Gene Expression by Antisense RNA of Mitochondrial Transcription Factor A (mtTFA)" 45(3) Biochemistry and Molecular Biology International 567-573 (Year: 1998).*
Japanese Office Action for Japanese Application No. 2017-552752, dated Dec. 1, 2020, 5 pages.
Rumi et al., "RNA Polymerase II Mediated Transcription from the Polymerase III Promoters in Short Hairpin RNA Expression Vector", Biochemical and Biophysical Research Communications, 339:610-17 (2006).

(Continued)

*Primary Examiner* — Nancy J Leith
(74) *Attorney, Agent, or Firm* — RatnerPrestia

(57) ABSTRACT

The problem to be solved is to provide a novel expression vector capable of effectively expressing a target protein in mitochondria and suppressing undesirable expression of the target protein in cell organelles other than mitochondria. The present invention provides a recombinant expression vector for expressing a target protein in mitochondria of animal cells, and a lipid membrane structure having the vector encapsulated therein, wherein the recombinant expression vector has a promoter sequence exhibiting a transcription activity in the nuclei of animal cells, and has, under the control of the promoter sequence, a coding region which codes a target protein and includes one or more TGAs as codons corresponding to tryptophan. The recombinant expression vector according to the present invention can more efficiently and selectively express a target protein in mitochondria, and can be used as a more safe and effective drug for treating mitochondrial diseases.

14 Claims, 5 Drawing Sheets

Specification includes a Sequence Listing.

(56) References Cited

FOREIGN PATENT DOCUMENTS

WO        2011132713  A1   10/2011
WO     WO 2011/132713     10/2011

OTHER PUBLICATIONS

Ishikawa et al., "Design of Artificial Mitrochondrial Reporter DNA Vector and Verification of Mitochondrial Gene Expression", Lecture abstract of Nucleic Acid Therapeutics Society of Japan 1st Annual Meeting with partial translation, 3 pages (2015).
International Search Report for International PCT Application No. PCT/JP2016/085098 dated Feb. 21, 2017.
Shaheen et al., Biomaterials, 32:6342-50 (2011).
Yu et al., PNAS, 109:E1238-47 (2012).
Extended European Search Report for European Application No. 16868706.9, dated Apr. 3, 2019, 9 pages.
Hyodo et al., Journal of Controlled Release, 193:316-23 (2014).
Ishikawa et al., Journal of Controlled Release, 274:109-17 (2018).
Jang and Lim, Molecules, 23(9):2316, pp. 1-16 (2018).
Sato et al., Advances in Genetics, 88:139-204 (2014).
Yamada et al., Biomaterials, 136:56-66 (2017).
Yasuzaki et al., Molecular Pharmaceutics, (12):4311-20 (2015).
OMIM "ATPase Inhibitory Factor 1: ATPIF1", Feb. 17, 2022, 2 pages.
Reyes et al., "Human Mitochondrial Transcription Factor A (mtTFA): Gene Structure and Characterization of Related Pseudogenes", Gene, 291(1-2):223-32 (2002), abstract.

* cited by examiner

SEQUENCE LISTING

```
<160> NUMBER OF SEQ ID NOS: 13

<210> SEQ ID NO 1
<211> LENGTH: 2645
<212> TYPE: DNA
<213> ORGANISM: Artificial Sequence
<220> FEATURE:
<223> OTHER INFORMATION: Synthesized DNA encoding a fusion protein
      consisting of ND4, FLAG tag and Luciferase
<220> FEATURE:
<221> NAME/KEY: CDS
<222> LOCATION: (583)..(2499)

<400> SEQUENCE: 1
ctgcagatta atagtaatca attacggggt cattagttca tagcccatat atggagttcc     60
gcgttacata acttacggta aatggcccgc ctggctgacc gcccaacgac ccccgcccat    120
tgacgtcaat aatgacgtat gttcccatag taacgccaat agggactttc cattgacgtc    180
aatgggtgga gtatttacgg taaactgccc acttggcagt acatcaagtg tatcatatgc    240
caagtccgcc ccctattgac gtcaatgacg gtaaatggcc cgcctggcat tatgcccagt    300
acatgacctt acgggacttt cctacttggc agtacatcta cgtattagtc atcgctatta    360
ccatgctgat gcggttttgg cagtacacca atgggcgtgg atagcggttt gactcacggg    420
gatttccaag tctccacccc attgacgtca atgggagttt gttttggcac caaaatcaac    480
gggactttcc aaaatgtcgt aataaccccg ccccgttgac gcaaatgggc ggtaggcgtg    540
tacggtggga ggtctatata agcagacgtc gtttagtgaa cc atg cta aaa att         594
                                                 Met Leu Lys Ile
                                                 1 att ctt ccc tca cta atg cta cta cca cta acc tga cta tca agc cct       642
Ile Leu Pro Ser Leu Met Leu Leu Pro Leu Thr Trp Leu Ser Ser Pro
5               10                  15                  20 aaa aaa acc tga aca aac gta acc tca tat agt ttt cta att agt tta       690
Lys Lys Thr Trp Thr Asn Val Thr Ser Tyr Ser Phe Leu Ile Ser Leu
            25                  30                  35 acc agc cta aca ctt cta tga caa acc gac gaa aat tat aaa aac ttt       738
Thr Ser Leu Thr Leu Leu Trp Gln Thr Asp Glu Asn Tyr Lys Asn Phe
        40                  45                  50 tca aat ata ttc tcc tca gac ccc cta tcc aca cca tta att att tta       786
Ser Asn Ile Phe Ser Ser Asp Pro Leu Ser Thr Pro Leu Ile Ile Leu
    55                  60                  65 aca gcc tga tta ctg cca cta ata tta ata gct agc caa aac cac cta       834
Thr Ala Trp Leu Leu Pro Leu Ile Leu Ile Ala Ser Gln Asn His Leu
70                  75                  80 aaa aaa gat aat aac gta cta caa aaa ctc tac atc tca ata cta atc       882
Lys Lys Asp Asn Asn Val Leu Gln Lys Leu Tyr Ile Ser Ile Leu Ile
85                  90                  95                 100 agc tta caa att ctc cta atc ata acc ttt tca gca act gaa cta att       930
Ser Leu Gln Ile Leu Leu Ile Ile Thr Phe Ser Ala Thr Glu Leu Ile
                105                 110                 115 ata ttt tat att tta ttt gaa gca acc tta atc cca aca ctt att att       978
Ile Phe Tyr Ile Leu Phe Glu Ala Thr Leu Ile Pro Thr Leu Ile Ile
                120                 125                 130
```

-continued

```
att acc cga tga ggg aac caa act gaa cgc cta aac gca ggg att tat    1026
Ile Thr Arg Trp Gly Asn Gln Thr Glu Arg Leu Asn Ala Gly Ile Tyr
        135                 140                 145 ttc cta ttt tat acc cta atc ggt tct att cca ctg cta att gcc ctc    1074
Phe Leu Phe Tyr Thr Leu Ile Gly Ser Ile Pro Leu Leu Ile Ala Leu
    150                 155                 160 atc tta atc caa aac cat gta gga acc cta aac ctc ata att tta tca    1122
Ile Leu Ile Gln Asn His Val Gly Thr Leu Asn Leu Ile Ile Leu Ser
165                 170                 175                 180 ttc aca aca cac acc tta gac gct tca tga tct aac aac tta cta tgg    1170
Phe Thr Thr His Thr Leu Asp Ala Ser Trp Ser Asn Asn Leu Leu Trp
            185                 190                 195 ttg gca tgc ata ata gca ttt ctt att aaa ata cca tta tat gga gtt    1218
Leu Ala Cys Ile Ile Ala Phe Leu Ile Lys Ile Pro Leu Tyr Gly Val
        200                 205                 210 cac cta tga cta cca aaa gcc cat gtt gaa gct cca att gct ggg tca    1266
His Leu Trp Leu Pro Lys Ala His Val Glu Ala Pro Ile Ala Gly Ser
    215                 220                 225 ata att cta gca gct att ctt cta aaa tta ggt agt tac gga ata att    1314
Ile Ile Leu Ala Ala Ile Leu Leu Lys Leu Gly Ser Tyr Gly Ile Ile
230                 235                 240 cgc atc tcc att att cta gac cca cta aca aaa tat ata gca tac ccc    1362
Arg Ile Ser Ile Ile Leu Asp Pro Leu Thr Lys Tyr Ile Ala Tyr Pro
245                 250                 255                 260 ttc atc ctt ctc tcc cta tga gga ata att ata act agc tca atc tgc    1410
Phe Ile Leu Leu Ser Leu Trp Gly Ile Ile Ile Thr Ser Ser Ile Cys
            265                 270                 275 tta cgc caa aca gat tta aaa tca cta atc gcc tac tcc tca gtt agc    1458
Leu Arg Gln Thr Asp Leu Lys Ser Leu Ile Ala Tyr Ser Ser Val Ser
        280                 285                 290 cac ata gca ctt gtt att gca tca atc ata atc caa act cca tga agc    1506
His Ile Ala Leu Val Ile Ala Ser Ile Ile Ile Gln Thr Pro Trp Ser
    295                 300                 305 ttc ata gga gca aca ata cta ata atc gca cat ggc ctc aca tca tca    1554
Phe Ile Gly Ala Thr Ile Leu Ile Ile Ala His Gly Leu Thr Ser Ser
310                 315                 320 ctc cta ttc tgc cta gca aac tcc aac tac gaa cgg atc cac agc cgt    1602
Leu Leu Phe Cys Leu Ala Asn Ser Asn Tyr Glu Arg Ile His Ser Arg
325                 330                 335                 340 act ata atc atg gcc cga gga ctt caa atg gtc ttc cca ctt ata gcc    1650
Thr Ile Ile Met Ala Arg Gly Leu Gln Met Val Phe Pro Leu Ile Ala
            345                 350                 355 aca tga tga ctg ata gca agt cta gct aat cta gct cta ccc cct tca    1698
Thr Trp Trp Leu Ile Ala Ser Leu Ala Asn Leu Ala Leu Pro Pro Ser
        360                 365                 370 atc aat cta ata gga gaa tta ttc att acc ata tca tta ttt tct tga    1746
Ile Asn Leu Ile Gly Glu Leu Phe Ile Thr Ile Ser Leu Phe Ser Trp
    375                 380                 385 tca aac ttt acc att att ctt ata gga att aac att att att aca ggt    1794
Ser Asn Phe Thr Ile Ile Leu Ile Gly Ile Asn Ile Ile Ile Thr Gly
390                 395                 400 ata tac tca ata tac ata att att acc acc caa cgc ggc aaa cta acc    1842
Ile Tyr Ser Ile Tyr Ile Ile Ile Thr Thr Gln Arg Gly Lys Leu Thr
405                 410                 415                 420 aac cat ata att aac ctc caa ccc tca cac aca cga gaa cta aca cta    1890
Asn His Ile Ile Asn Leu Gln Pro Ser His Thr Arg Glu Leu Thr Leu
            425                 430                 435 ata gcc ctt cac ata att cca ctt att ctt cta act acc aat cca aaa    1938
Ile Ala Leu His Ile Ile Pro Leu Ile Leu Leu Thr Thr Asn Pro Lys
```

-continued

```
                440             445             450
cta att aca ggc ctg aca ata gat tac aag gat gac gac gat aag atg    1986
Leu Ile Thr Gly Leu Thr Ile Asp Tyr Lys Asp Asp Asp Asp Lys Met
            455             460             465 gtc ttc aca ctc gaa gat ttc gtt ggg gac tga cga cag aca gcc ggc    2034
Val Phe Thr Leu Glu Asp Phe Val Gly Asp Trp Arg Gln Thr Ala Gly
    470             475             480 tac aac ctg gac caa gtc ctt gaa cag gga ggt gtg tcc agt ttg ttt    2082
Tyr Asn Leu Asp Gln Val Leu Glu Gln Gly Gly Val Ser Ser Leu Phe
485             490             495             500 cag aat ctc ggg gtg tcc gta act ccg atc caa cgg att gtc ctg agc    2130
Gln Asn Leu Gly Val Ser Val Thr Pro Ile Gln Arg Ile Val Leu Ser
                505             510             515 ggt gaa aat ggg ctg aag atc gac atc cat gtc atc atc ccg tat gaa    2178
Gly Glu Asn Gly Leu Lys Ile Asp Ile His Val Ile Ile Pro Tyr Glu
            520             525             530 ggt ctg agc ggc gac caa atg ggc cag atc gaa aaa att ttt aag gtg    2226
Gly Leu Ser Gly Asp Gln Met Gly Gln Ile Glu Lys Ile Phe Lys Val
        535             540             545 gtg tac cct gtg gat gat cat cac ttt aag gtg atc ctg cac tat ggc    2274
Val Tyr Pro Val Asp Asp His His Phe Lys Val Ile Leu His Tyr Gly
    550             555             560 aca ctg gta atc gac ggg gtt acg ccg aac atg atc gat tat ttc gga    2322
Thr Leu Val Ile Asp Gly Val Thr Pro Asn Met Ile Asp Tyr Phe Gly
565             570             575             580 cgg ccg tat gaa ggc atc gcc gtg ttc gac ggc aaa aag atc act gta    2370
Arg Pro Tyr Glu Gly Ile Ala Val Phe Asp Gly Lys Lys Ile Thr Val
                585             590             595 aca ggg acc ctg tgg aac ggc aac aaa att atc gac gag cgc ctg atc    2418
Thr Gly Thr Leu Trp Asn Gly Asn Lys Ile Ile Asp Glu Arg Leu Ile
            600             605             610 aac ccc gac ggc tcc ctg ctg ttc cga gta acc atc aac gga gtg acc    2466
Asn Pro Asp Gly Ser Leu Leu Phe Arg Val Thr Ile Asn Gly Val Thr
        615             620             625 ggc tgg cgg ctg tgc gaa cgc att ctg gcg taa gaaaggaagg aatcgaaccc  2519
Gly Trp Arg Leu Cys Glu Arg Ile Leu Ala
    630             635 cctaaaattg gtttcaagcc aatctcatat cctatatgtc tttctcaata agatattagt  2579
aaaatcaatt acataacttt gtcaaagtta aattatagat caataatcta tatatcttat  2639
ctgcag                                                              2645
```

<210> SEQ ID NO 2
<211> LENGTH: 638
<212> TYPE: PRT
<213> ORGANISM: Artificial Sequence
<220> FEATURE:
<223> OTHER INFORMATION: Synthetic Construct

<400> SEQUENCE: 2

```
Met Leu Lys Ile Ile Leu Pro Ser Leu Met Leu Leu Pro Leu Thr Trp
1               5                   10                  15

Leu Ser Ser Pro Lys Lys Thr Trp Thr Asn Val Thr Ser Tyr Ser Phe
            20                  25                  30

Leu Ile Ser Leu Thr Ser Leu Thr Leu Leu Trp Gln Thr Asp Glu Asn
        35                  40                  45

Tyr Lys Asn Phe Ser Asn Ile Phe Ser Ser Asp Pro Leu Ser Thr Pro
    50                  55                  60

Leu Ile Ile Leu Thr Ala Trp Leu Leu Pro Leu Ile Leu Ile Ala Ser
```

-continued

```
            65                  70                  75                  80
        Gln Asn His Leu Lys Lys Asp Asn Val Leu Gln Lys Leu Tyr Ile
                            85                  90                  95
        Ser Ile Leu Ile Ser Leu Gln Ile Leu Leu Ile Ile Thr Phe Ser Ala
                           100                 105                 110
        Thr Glu Leu Ile Ile Phe Tyr Ile Leu Phe Glu Ala Thr Leu Ile Pro
                           115                 120                 125
        Thr Leu Ile Ile Ile Thr Arg Trp Gly Asn Gln Thr Glu Arg Leu Asn
                   130                 135                 140
        Ala Gly Ile Tyr Phe Leu Phe Tyr Thr Leu Ile Gly Ser Ile Pro Leu
        145                 150                 155                 160
        Leu Ile Ala Leu Ile Leu Ile Gln Asn His Val Gly Thr Leu Asn Leu
                       165                 170                 175
        Ile Ile Leu Ser Phe Thr Thr His Thr Leu Asp Ala Ser Trp Ser Asn
                       180                 185                 190
        Asn Leu Leu Trp Leu Ala Cys Ile Ile Ala Phe Leu Ile Lys Ile Pro
                       195                 200                 205
        Leu Tyr Gly Val His Leu Trp Leu Pro Lys Ala His Val Glu Ala Pro
                       210                 215                 220
        Ile Ala Gly Ser Ile Ile Leu Ala Ala Ile Leu Leu Lys Leu Gly Ser
        225                 230                 235                 240
        Tyr Gly Ile Ile Arg Ile Ser Ile Ile Leu Asp Pro Leu Thr Lys Tyr
                       245                 250                 255
        Ile Ala Tyr Pro Phe Ile Leu Leu Ser Leu Trp Gly Ile Ile Ile Thr
                       260                 265                 270
        Ser Ser Ile Cys Leu Arg Gln Thr Asp Leu Lys Ser Leu Ile Ala Tyr
                       275                 280                 285
        Ser Ser Val Ser His Ile Ala Leu Val Ile Ala Ser Ile Ile Ile Gln
                       290                 295                 300
        Thr Pro Trp Ser Phe Ile Gly Ala Thr Ile Leu Ile Ile Ala His Gly
        305                 310                 315                 320
        Leu Thr Ser Ser Leu Leu Phe Cys Leu Ala Asn Ser Asn Tyr Glu Arg
                       325                 330                 335
        Ile His Ser Arg Thr Ile Ile Met Ala Arg Gly Leu Gln Met Val Phe
                       340                 345                 350
        Pro Leu Ile Ala Thr Trp Trp Leu Ile Ala Ser Leu Ala Asn Leu Ala
                       355                 360                 365
        Leu Pro Pro Ser Ile Asn Leu Ile Gly Glu Leu Phe Ile Thr Ile Ser
                       370                 375                 380
        Leu Phe Ser Trp Ser Asn Phe Thr Ile Ile Leu Ile Gly Ile Asn Ile
        385                 390                 395                 400
        Ile Ile Thr Gly Ile Tyr Ser Ile Tyr Ile Ile Thr Thr Gln Arg
                       405                 410                 415
        Gly Lys Leu Thr Asn His Ile Ile Asn Leu Gln Pro Ser His Thr Arg
                       420                 425                 430
        Glu Leu Thr Leu Ile Ala Leu His Ile Ile Pro Leu Ile Leu Leu Thr
                       435                 440                 445
        Thr Asn Pro Lys Leu Ile Thr Gly Leu Thr Ile Asp Tyr Lys Asp Asp
                       450                 455                 460
        Asp Asp Lys Met Val Phe Thr Leu Glu Asp Phe Val Gly Asp Trp Arg
        465                 470                 475                 480
        Gln Thr Ala Gly Tyr Asn Leu Asp Gln Val Leu Glu Gln Gly Gly Val
                       485                 490                 495
```

```
Ser Ser Leu Phe Gln Asn Leu Gly Val Ser Val Thr Pro Ile Gln Arg
            500                 505                 510

Ile Val Leu Ser Gly Glu Asn Gly Leu Lys Ile Asp Ile His Val Ile
            515                 520                 525

Ile Pro Tyr Glu Gly Leu Ser Gly Asp Gln Met Gly Gln Ile Glu Lys
            530                 535                 540

Ile Phe Lys Val Val Tyr Pro Val Asp His His Phe Lys Val Ile
545                 550                 555                 560

Leu His Tyr Gly Thr Leu Val Ile Asp Gly Val Thr Pro Asn Met Ile
            565                 570                 575

Asp Tyr Phe Gly Arg Pro Tyr Glu Gly Ile Ala Val Phe Asp Gly Lys
            580                 585                 590

Lys Ile Thr Val Thr Gly Thr Leu Trp Asn Gly Asn Lys Ile Ile Asp
            595                 600                 605

Glu Arg Leu Ile Asn Pro Asp Gly Ser Leu Leu Phe Arg Val Thr Ile
            610                 615                 620

Asn Gly Val Thr Gly Trp Arg Leu Cys Glu Arg Ile Leu Ala
625                 630                 635

<210> SEQ ID NO 3
<211> LENGTH: 2645
<212> TYPE: DNA
<213> ORGANISM: Artificial Sequence
<220> FEATURE:
<223> OTHER INFORMATION: Synthesized DNA encoding a fusion protein
      comprising ND4, FLAG Tag and Luciferase
<220> FEATURE:
<221> NAME/KEY: CDS
<222> LOCATION: (583)..(2499)

<400> SEQUENCE: 3
ctgcagatta atagtaatca attacggggt cattagttca tagcccatat atggagttcc    60
gcgttacata acttcggta aatggcccgc ctggctgacc gcccaacgac ccccgcccat    120
tgacgtcaat aatgacgtat gttcccatag taacgccaat agggactttc cattgacgtc    180
aatgggtgga gtatttacgg taaactgccc acttggcagt acatcaagtg tatcatatgc    240
caagtccgcc ccctattgac gtcaatgacg gtaaatggcc cgcctggcat tatgcccagt    300
acatgacctt acgggacttt cctacttggc agtacatcta cgtattagtc atcgctatta    360
ccatgctgat gcggttttgg cagtacacca atgggcgtgg atagcggttt gactcacggg    420
gatttccaag tctccacccc attgacgtca atgggagttt gttttggcac caaaatcaac    480
gggactttcc aaaatgtcgt aataaccccg ccccgttgac gcaaatgggc ggtaggcgtg    540
tacggtggga ggtctatata agcagacgtc gtttagtgaa cc atg cta aaa att        594
                                                Met Leu Lys Ile
                                                1 att ctt ccc tca cta atg cta cta cca cta acc tga cta tca agc cct        642
Ile Leu Pro Ser Leu Met Leu Leu Pro Leu Thr Trp Leu Ser Ser Pro
5                   10                  15                  20 aaa aaa acc tga aca aac gta acc tca tat agt ttt cta att agt tta        690
Lys Lys Thr Trp Thr Asn Val Thr Ser Tyr Ser Phe Leu Ile Ser Leu
                25                  30                  35 acc agc cta aca ctt cta tga caa acc gac gaa aat tat aaa aac ttt        738
Thr Ser Leu Thr Leu Leu Trp Gln Thr Asp Glu Asn Tyr Lys Asn Phe
            40                  45                  50 tca aat ata ttc tcc tca gac ccc cta tcc aca cca tta att att tta        786
Ser Asn Ile Phe Ser Ser Asp Pro Leu Ser Thr Pro Leu Ile Ile Leu
        55                  60                  65
```

```
aca gcc tga tta ctg cca cta ata tta ata gct agc caa aac cac cta      834
Thr Ala Trp Leu Leu Pro Leu Ile Leu Ile Ala Ser Gln Asn His Leu
    70              75                  80 aaa aaa gat aat aac gta cta caa aaa ctc tac atc tca ata cta atc      882
Lys Lys Asp Asn Asn Val Leu Gln Lys Leu Tyr Ile Ser Ile Leu Ile
85              90                  95                  100 agc tta caa att ctc cta atc ata acc ttt tca gca act gaa cta att      930
Ser Leu Gln Ile Leu Leu Ile Ile Thr Phe Ser Ala Thr Glu Leu Ile
                105                 110                 115 ata ttt tat att tta ttt gaa gca acc tta atc cca aca ctt att att      978
Ile Phe Tyr Ile Leu Phe Glu Ala Thr Leu Ile Pro Thr Leu Ile Ile
            120                 125                 130 att acc cga tga ggg aac caa act gaa cgc cta aac gca ggg att tat     1026
Ile Thr Arg Trp Gly Asn Gln Thr Glu Arg Leu Asn Ala Gly Ile Tyr
        135                 140                 145 ttc cta ttt tat acc cta atc ggt tct att cca ctg cta att gcc ctc     1074
Phe Leu Phe Tyr Thr Leu Ile Gly Ser Ile Pro Leu Leu Ile Ala Leu
    150                 155                 160 atc tta atc caa aac cat gta gga acc cta aac ctc ata att tta tca     1122
Ile Leu Ile Gln Asn His Val Gly Thr Leu Asn Leu Ile Ile Leu Ser
165                 170                 175                 180 ttc aca aca cac acc tta gac gct tca tga tct aac aac tta cta tgg     1170
Phe Thr Thr His Thr Leu Asp Ala Ser Trp Ser Asn Asn Leu Leu Trp
                185                 190                 195 ttg gca tgc ata ata gca ttt ctt att aaa ata cca tta tat gga gtt     1218
Leu Ala Cys Ile Ile Ala Phe Leu Ile Lys Ile Pro Leu Tyr Gly Val
            200                 205                 210 cac cta tga cta cca aaa gcc cat gtt gaa gct cca att gct ggg tca     1266
His Leu Trp Leu Pro Lys Ala His Val Glu Ala Pro Ile Ala Gly Ser
        215                 220                 225 ata att cta gca gct att ctt cta aaa tta ggt agt tac gga ata att     1314
Ile Ile Leu Ala Ala Ile Leu Leu Lys Leu Gly Ser Tyr Gly Ile Ile
230                 235                 240 cgc atc tcc att att cta gac cca cta aca aaa tat ata gca tac ccc     1362
Arg Ile Ser Ile Ile Leu Asp Pro Leu Thr Lys Tyr Ile Ala Tyr Pro
245                 250                 255                 260 ttc atc ctt ctc tcc cta tga gga ata att ata act agc tca atc tgc     1410
Phe Ile Leu Leu Ser Leu Trp Gly Ile Ile Ile Thr Ser Ser Ile Cys
                265                 270                 275 tta cgc caa aca gat tta aaa tca cta atc gcc tac tca tca gtt agc     1458
Leu Arg Gln Thr Asp Leu Lys Ser Leu Ile Ala Tyr Ser Ser Val Ser
            280                 285                 290 cac ata gca ctt gtt att gca tca atc ata atc caa act cca tga agc     1506
His Ile Ala Leu Val Ile Ala Ser Ile Ile Ile Gln Thr Pro Trp Ser
        295                 300                 305 ttc ata gga gca aca ata cta ata atc gca cat ggc ctc aca tca tca     1554
Phe Ile Gly Ala Thr Ile Leu Ile Ile Ala His Gly Leu Thr Ser Ser
310                 315                 320 ctc cta ttc tgc cta gca aac tcc aac tac gaa cgg atc cac agc cgt     1602
Leu Leu Phe Cys Leu Ala Asn Ser Asn Tyr Glu Arg Ile His Ser Arg
325                 330                 335                 340 act ata atc atg gcc cga gga ctt caa atg gtc ttc cca ctt ata gcc     1650
Thr Ile Ile Met Ala Arg Gly Leu Gln Met Val Phe Pro Leu Ile Ala
                345                 350                 355 aca tga tga ctg ata gca agt cta gct aat cta gct cta ccc cct tca     1698
Thr Trp Trp Leu Ile Ala Ser Leu Ala Asn Leu Ala Leu Pro Pro Ser
            360                 365                 370 atc aat cta ata gga gaa tta ttc att acc ata tca tta ttt tct tga     1746
Ile Asn Leu Ile Gly Glu Leu Phe Ile Thr Ile Ser Leu Phe Ser Trp
```

```
              375                 380                 385
tca aac ttt acc att att ctt ata gga att aac att att att aca ggt    1794
Ser Asn Phe Thr Ile Ile Leu Ile Gly Ile Asn Ile Ile Ile Thr Gly
    390                 395                 400 ata tac tca ata tac ata att att acc acc caa cgc ggc aaa cta acc    1842
Ile Tyr Ser Ile Tyr Ile Ile Ile Thr Thr Gln Arg Gly Lys Leu Thr
405                 410                 415                 420 aac cat ata att aac ctc caa ccc tca cac aca cga gaa cta aca cta    1890
Asn His Ile Ile Asn Leu Gln Pro Ser His Thr Arg Glu Leu Thr Leu
            425                 430                 435 ata gcc ctt cac ata att cca ctt att ctt cta act acc aat cca aaa    1938
Ile Ala Leu His Ile Ile Pro Leu Ile Leu Leu Thr Thr Asn Pro Lys
        440                 445                 450 cta att aca ggc ctg aca ata gat tac aag gat gac gac gat aag atg    1986
Leu Ile Thr Gly Leu Thr Ile Asp Tyr Lys Asp Asp Asp Asp Lys Met
    455                 460                 465 gtc ttc aca ctc gaa gat ttc gtt ggg gac tga cga cag aca gcc ggc    2034
Val Phe Thr Leu Glu Asp Phe Val Gly Asp Trp Arg Gln Thr Ala Gly
470                 475                 480 tac aac ctg gac caa gtc ctt gaa cag gga ggt gtg tcc agt ttg ttt    2082
Tyr Asn Leu Asp Gln Val Leu Glu Gln Gly Gly Val Ser Ser Leu Phe
485                 490                 495                 500 cag aat ctc ggg gtg tcc gta act ccg atc caa cgg att gtc ctg agc    2130
Gln Asn Leu Gly Val Ser Val Thr Pro Ile Gln Arg Ile Val Leu Ser
            505                 510                 515 ggt gaa aat ggg ctg aag atc gac atc cat gtc atc atc ccg tat gaa    2178
Gly Glu Asn Gly Leu Lys Ile Asp Ile His Val Ile Ile Pro Tyr Glu
        520                 525                 530 ggt ctg agc ggc gac caa atg ggc cag atc gaa aaa att ttt aag gtg    2226
Gly Leu Ser Gly Asp Gln Met Gly Gln Ile Glu Lys Ile Phe Lys Val
    535                 540                 545 gtg tac cct gtg gat gat cat cac ttt aag gtg atc ctg cac tat ggc    2274
Val Tyr Pro Val Asp Asp His His Phe Lys Val Ile Leu His Tyr Gly
550                 555                 560 aca ctg gta atc gac ggg gtt acg ccg aac atg atc gac tat ttc gga    2322
Thr Leu Val Ile Asp Gly Val Thr Pro Asn Met Ile Asp Tyr Phe Gly
565                 570                 575                 580 cgg ccg tat gaa ggc atc gcc gtg ttc gac ggc aaa aag atc act gta    2370
Arg Pro Tyr Glu Gly Ile Ala Val Phe Asp Gly Lys Lys Ile Thr Val
            585                 590                 595 aca ggg acc ctg tga aac ggc aac aaa att atc gac gag cgc ctg atc    2418
Thr Gly Thr Leu Trp Asn Gly Asn Lys Ile Ile Asp Glu Arg Leu Ile
        600                 605                 610 aac ccc gac ggc tcc ctg ctg ttc cga gta acc atc aac gga gtg acc    2466
Asn Pro Asp Gly Ser Leu Leu Phe Arg Val Thr Ile Asn Gly Val Thr
    615                 620                 625 ggc tga cgg ctg tgc gaa cgc att ctg gcg taa gaaaggaagg aatcgaaccc  2519
Gly Trp Arg Leu Cys Glu Arg Ile Leu Ala
630                 635 cctaaaattg gtttcaagcc aatctcatat cctatatgtc tttctcaata agatattagt  2579
aaaatcaatt acataacttt gtcaaagtta aattatagat caataatcta tatatcttat  2639
ctgcag                                                              2645

<210> SEQ ID NO 4
<211> LENGTH: 638
<212> TYPE: PRT
<213> ORGANISM: Artificial Sequence
<220> FEATURE:
<223> OTHER INFORMATION: Synthetic Construct
```

-continued

```
<400> SEQUENCE: 4

Met Leu Lys Ile Ile Leu Pro Ser Leu Met Leu Leu Pro Leu Thr Trp
1               5                   10                  15

Leu Ser Ser Pro Lys Lys Thr Trp Thr Asn Val Thr Ser Tyr Ser Phe
            20                  25                  30

Leu Ile Ser Leu Thr Ser Leu Thr Leu Leu Trp Gln Thr Asp Glu Asn
        35                  40                  45

Tyr Lys Asn Phe Ser Asn Ile Phe Ser Ser Asp Pro Leu Ser Thr Pro
    50                  55                  60

Leu Ile Ile Leu Thr Ala Trp Leu Leu Pro Leu Ile Leu Ile Ala Ser
65                  70                  75                  80

Gln Asn His Leu Lys Lys Asp Asn Asn Val Leu Gln Lys Leu Tyr Ile
                85                  90                  95

Ser Ile Leu Ile Ser Leu Gln Ile Leu Leu Ile Ile Thr Phe Ser Ala
            100                 105                 110

Thr Glu Leu Ile Ile Phe Tyr Ile Leu Phe Glu Ala Thr Leu Ile Pro
        115                 120                 125

Thr Leu Ile Ile Ile Thr Arg Trp Gly Asn Gln Thr Glu Arg Leu Asn
130                 135                 140

Ala Gly Ile Tyr Phe Leu Phe Tyr Thr Leu Ile Gly Ser Ile Pro Leu
145                 150                 155                 160

Leu Ile Ala Leu Ile Leu Ile Gln Asn His Val Gly Thr Leu Asn Leu
                165                 170                 175

Ile Ile Leu Ser Phe Thr Thr His Thr Leu Asp Ala Ser Trp Ser Asn
            180                 185                 190

Asn Leu Leu Trp Leu Ala Cys Ile Ile Ala Phe Leu Ile Lys Ile Pro
        195                 200                 205

Leu Tyr Gly Val His Leu Trp Leu Pro Lys Ala His Val Glu Ala Pro
    210                 215                 220

Ile Ala Gly Ser Ile Ile Leu Ala Ala Ile Leu Leu Lys Leu Gly Ser
225                 230                 235                 240

Tyr Gly Ile Ile Arg Ile Ser Ile Ile Leu Asp Pro Leu Thr Lys Tyr
                245                 250                 255

Ile Ala Tyr Pro Phe Ile Leu Leu Ser Leu Trp Gly Ile Ile Ile Thr
            260                 265                 270

Ser Ser Ile Cys Leu Arg Gln Thr Asp Leu Lys Ser Leu Ile Ala Tyr
        275                 280                 285

Ser Ser Val Ser His Ile Ala Leu Val Ile Ala Ser Ile Ile Ile Gln
    290                 295                 300

Thr Pro Trp Ser Phe Ile Gly Ala Thr Ile Leu Ile Ile Ala His Gly
305                 310                 315                 320

Leu Thr Ser Ser Leu Leu Phe Cys Leu Ala Asn Ser Asn Tyr Glu Arg
                325                 330                 335

Ile His Ser Arg Thr Ile Ile Met Ala Arg Gly Leu Gln Met Val Phe
            340                 345                 350

Pro Leu Ile Ala Thr Trp Trp Leu Ile Ala Ser Leu Ala Asn Leu Ala
        355                 360                 365

Leu Pro Pro Ser Ile Asn Leu Ile Gly Glu Leu Phe Ile Thr Ile Ser
    370                 375                 380

Leu Phe Ser Trp Ser Asn Phe Thr Ile Ile Leu Ile Gly Ile Asn Ile
385                 390                 395                 400

Ile Ile Thr Gly Ile Tyr Ser Ile Tyr Ile Ile Ile Thr Thr Gln Arg
```

|  |  |  | 405 |  |  |  |  | 410 |  |  |  |  | 415 |  |  |
|---|---|---|---|---|---|---|---|---|---|---|---|---|---|---|---|

Gly Lys Leu Thr Asn His Ile Ile Asn Leu Gln Pro Ser His Thr Arg
            420                 425                 430

Glu Leu Thr Leu Ile Ala Leu His Ile Ile Pro Leu Ile Leu Leu Thr
            435                 440                 445

Thr Asn Pro Lys Leu Ile Thr Gly Leu Thr Ile Asp Tyr Lys Asp Asp
450                 455                 460

Asp Asp Lys Met Val Phe Thr Leu Glu Asp Phe Val Gly Asp Trp Arg
465                 470                 475                 480

Gln Thr Ala Gly Tyr Asn Leu Asp Gln Val Leu Glu Gln Gly Gly Val
                485                 490                 495

Ser Ser Leu Phe Gln Asn Leu Gly Val Ser Val Thr Pro Ile Gln Arg
                500                 505                 510

Ile Val Leu Ser Gly Glu Asn Gly Leu Lys Ile Asp Ile His Val Ile
                515                 520                 525

Ile Pro Tyr Glu Gly Leu Ser Gly Asp Gln Met Gly Gln Ile Glu Lys
530                 535                 540

Ile Phe Lys Val Val Tyr Pro Val Asp Asp His His Phe Lys Val Ile
545                 550                 555                 560

Leu His Tyr Gly Thr Leu Val Ile Asp Gly Val Thr Pro Asn Met Ile
                565                 570                 575

Asp Tyr Phe Gly Arg Pro Tyr Glu Gly Ile Ala Val Phe Asp Gly Lys
                580                 585                 590

Lys Ile Thr Val Thr Gly Thr Leu Trp Asn Gly Asn Lys Ile Ile Asp
                595                 600                 605

Glu Arg Leu Ile Asn Pro Asp Gly Ser Leu Leu Phe Arg Val Thr Ile
            610                 615                 620

Asn Gly Val Thr Gly Trp Arg Leu Cys Glu Arg Ile Leu Ala
625                 630                 635

<210> SEQ ID NO 5
<211> LENGTH: 2645
<212> TYPE: DNA
<213> ORGANISM: Artificial Sequence
<220> FEATURE:
<223> OTHER INFORMATION: Synthesized DNA encoding a fusion protein
      comprising ND4, FLAG Tag and Luciferase
<220> FEATURE:
<221> NAME/KEY: CDS
<222> LOCATION: (583)..(2118)

<400> SEQUENCE: 5
ctgcagatta atagtaatca attacggggt cattagttca tagcccatat atggagttcc      60
gcgttacata acttacggta aatggcccgc ctggctgacc gcccaacgac ccccgcccat     120
tgacgtcaat aatgacgtat gttcccatag taacgccaat agggactttc cattgacgtc     180
aatgggtgga gtatttacgg taaactgccc acttggcagt acatcaagtg tatcatatgc     240
caagtccgcc ccctattgac gtcaatgacg gtaaatggcc cgcctggcat tatgcccagt     300
acatgacctt acgggacttt cctacttggc agtacatcta cgtattagtc atcgctatta     360
ccatgctgat gcggttttgg cagtacacca atgggcgtgg atagcggttt gactcacggg     420
gatttccaag tctccacccc attgacgtca atgggagttt gttttggcac caaaatcaac     480
gggactttcc aaaatgtcgt aataaccccg ccccgttgac gcaaatgggc ggtaggcgtg     540
tacggtggga ggtctatata agcagacgtc gtttagtgaa cc atg cta aaa att        594
                                               Met Leu Lys Ile
                                                 1

| | |
|---|---|
| att ctt ccc tca cta atg cta cta cca cta acc tga cta tca agc cct<br>Ile Leu Pro Ser Leu Met Leu Leu Pro Leu Thr Trp Leu Ser Ser Pro<br>5                              10                          15                  20 | 642 |
| aaa aaa acc tga aca aac gta acc tca tat agt ttt cta att agt tta<br>Lys Lys Thr Trp Thr Asn Val Thr Ser Tyr Ser Phe Leu Ile Ser Leu<br>                  25                          30                          35 | 690 |
| acc agc cta aca ctt cta tga caa acc gac gaa aat tat aaa aac ttt<br>Thr Ser Leu Thr Leu Leu Trp Gln Thr Asp Glu Asn Tyr Lys Asn Phe<br>             40                          45                          50 | 738 |
| tca aat ata ttc tcc tca gac ccc cta tcc aca cca tta att att tta<br>Ser Asn Ile Phe Ser Ser Asp Pro Leu Ser Thr Pro Leu Ile Ile Leu<br>             55                          60                          65 | 786 |
| aca gcc tga tta ctg cca cta ata tta ata gct agc caa aac cac cta<br>Thr Ala Trp Leu Leu Pro Leu Ile Leu Ile Ala Ser Gln Asn His Leu<br>             70                          75                          80 | 834 |
| aaa aaa gat aat aac gta cta caa aaa ctc tac atc tca ata cta atc<br>Lys Lys Asp Asn Asn Val Leu Gln Lys Leu Tyr Ile Ser Ile Leu Ile<br>85                              90                          95                        100 | 882 |
| agc tta caa att ctc cta atc ata acc ttt tca gca act gaa cta att<br>Ser Leu Gln Ile Leu Leu Ile Ile Thr Phe Ser Ala Thr Glu Leu Ile<br>                  105                       110                      115 | 930 |
| ata ttt tat att tta ttt gaa gca acc tta atc cca aca ctt att att<br>Ile Phe Tyr Ile Leu Phe Glu Ala Thr Leu Ile Pro Thr Leu Ile Ile<br>                  120                       125                      130 | 978 |
| att acc cga tga ggg aac caa act gaa cgc cta aac gca ggg att tat<br>Ile Thr Arg Trp Gly Asn Gln Thr Glu Arg Leu Asn Ala Gly Ile Tyr<br>             135                        140                        145 | 1026 |
| ttc cta ttt tat acc cta atc ggt tct att cca ctg cta att gcc ctc<br>Phe Leu Phe Tyr Thr Leu Ile Gly Ser Ile Pro Leu Leu Ile Ala Leu<br>                  150                       155                      160 | 1074 |
| atc tta atc caa aac cat gta gga acc cta aac ctc ata att tta tca<br>Ile Leu Ile Gln Asn His Val Gly Thr Leu Asn Leu Ile Ile Leu Ser<br>165                            170                        175                        180 | 1122 |
| ttc aca aca cac acc tta gac gct tca tga tct aac aac tta cta tgg<br>Phe Thr Thr His Thr Leu Asp Ala Ser Trp Ser Asn Asn Leu Leu Trp<br>                  185                       190                      195 | 1170 |
| ttg gca tgc ata ata gca ttt ctt att aaa ata cca tta tat gga gtt<br>Leu Ala Cys Ile Ile Ala Phe Leu Ile Lys Ile Pro Leu Tyr Gly Val<br>             200                        205                        210 | 1218 |
| cac cta tga cta cca aaa gcc cat gtt gaa gct cca att gct ggg tca<br>His Leu Trp Leu Pro Lys Ala His Val Glu Ala Pro Ile Ala Gly Ser<br>                  215                       220                      225 | 1266 |
| ata att cta gca gct att ctt cta aaa tta ggt agt tac gga ata att<br>Ile Ile Leu Ala Ala Ile Leu Leu Lys Leu Gly Ser Tyr Gly Ile Ile<br>             230                        235                        240 | 1314 |
| cgc atc tcc att att cta gac cca cta aca aaa tat ata gca tac ccc<br>Arg Ile Ser Ile Ile Leu Asp Pro Leu Thr Lys Tyr Ile Ala Tyr Pro<br>245                            250                        255                        260 | 1362 |
| ttc atc ctt ctc tcc cta tga gga ata att ata act agc tca atc tgc<br>Phe Ile Leu Leu Ser Leu Trp Gly Ile Ile Ile Thr Ser Ser Ile Cys<br>                  265                       270                      275 | 1410 |
| tta cgc caa aca gat tta aaa tca cta atc gcc tac tcc tca gtt agc<br>Leu Arg Gln Thr Asp Leu Lys Ser Leu Ile Ala Tyr Ser Ser Val Ser<br>             280                        285                        290 | 1458 |
| cac ata gca ctt gtt att gca tca atc ata atc caa act cca tga agc<br>His Ile Ala Leu Val Ile Ala Ser Ile Ile Ile Gln Thr Pro Trp Ser<br>                  295                       300                      305 | 1506 |
| ttc ata gga gca aca ata cta ata atc gca cat ggc ctc aca tca tca<br>Phe Ile Gly Ala Thr Ile Leu Ile Ile Ala His Gly Leu Thr Ser Ser | 1554 |

```
                    310                 315                 320
ctc cta ttc tgc cta gca aac tcc aac tac gaa cgg atc cac agc cgt    1602
Leu Leu Phe Cys Leu Ala Asn Ser Asn Tyr Glu Arg Ile His Ser Arg
325                 330                 335                 340 act ata atc atg gcc cga gga ctt caa atg gtc ttc cca ctt ata gcc    1650
Thr Ile Ile Met Ala Arg Gly Leu Gln Met Val Phe Pro Leu Ile Ala
                345                 350                 355 aca tga tga ctg ata gca agt cta gct aat cta gct cta ccc cct tca    1698
Thr Trp Trp Leu Ile Ala Ser Leu Ala Asn Leu Ala Leu Pro Pro Ser
            360                 365                 370 atc aat cta ata gga gaa tta ttc att acc ata tca tta ttt tct tga    1746
Ile Asn Leu Ile Gly Glu Leu Phe Ile Thr Ile Ser Leu Phe Ser Trp
        375                 380                 385 tca aac ttt acc att att ctt ata gga att aac att att att aca ggt    1794
Ser Asn Phe Thr Ile Ile Leu Ile Gly Ile Asn Ile Ile Ile Thr Gly
    390                 395                 400 ata tac tca ata tac ata att att acc acc caa cgc ggc aaa cta acc    1842
Ile Tyr Ser Ile Tyr Ile Ile Ile Thr Thr Gln Arg Gly Lys Leu Thr
405                 410                 415                 420 aac cat ata att aac ctc caa ccc tca cac aca cga gaa cta aca cta    1890
Asn His Ile Ile Asn Leu Gln Pro Ser His Thr Arg Glu Leu Thr Leu
                425                 430                 435 ata gcc ctt cac ata att cca ctt att ctt cta act acc aat cca aaa    1938
Ile Ala Leu His Ile Ile Pro Leu Ile Leu Leu Thr Thr Asn Pro Lys
            440                 445                 450 cta att aca ggc ctg aca ata gat tac aag gat gac gac gat aag atg    1986
Leu Ile Thr Gly Leu Thr Ile Asp Tyr Lys Asp Asp Asp Asp Lys Met
        455                 460                 465 gtc ttc aca ctc gaa gat ttc gtt ggg gac tga cga cag aca gcc ggc    2034
Val Phe Thr Leu Glu Asp Phe Val Gly Asp Trp Arg Gln Thr Ala Gly
    470                 475                 480 tac aac ctg gac caa gtc ctt gaa cag gga ggt gtg tcc agt ttg ttt    2082
Tyr Asn Leu Asp Gln Val Leu Glu Gln Gly Gly Val Ser Ser Leu Phe
485                 490                 495                 500 cag aat ctc ggg gtg tcc gta act ccg atc caa tag attgtcctga         2128
Gln Asn Leu Gly Val Ser Val Thr Pro Ile Gln
                505                 510 gcggtgaaaa tgggctgaag atcgacatcc atgtcatcat cccgtatgaa ggtctgagcg  2188
gcgaccaaat gggccagatc gaaaaaattt ttaaggtggt gtaccctgtg gatgatcatc  2248
actttaaggt gatcctgcac tatggcacac tggtaatcga cggggttacg ccgaacatga  2308
tcgactattt cggacggccg tatgaaggca tcgccgtgtt cgacggcaaa agatcactg   2368 taacagggac cctgtggaac ggcaacaaaa ttatcgacga gcgcctgatc aaccccgacg  2428
gctccctgct gttccgagta accatcaacg gagtgaccgg ctggcggctg tgcgaacgca  2488
ttctggcgta agaaaggaag gaatcgaacc ccctaaaatt ggtttcaagc caatctcata  2548
tcctatatgt ctttctcaat aagatattag taaaatcaat tacataactt tgtcaaagtt  2608
aaattataga tcaataatct atatatctta tctgcag                           2645

<210> SEQ ID NO 6
<211> LENGTH: 511
<212> TYPE: PRT
<213> ORGANISM: Artificial Sequence
<220> FEATURE:
<223> OTHER INFORMATION: Synthetic Construct

<400> SEQUENCE: 6

Met Leu Lys Ile Ile Leu Pro Ser Leu Met Leu Leu Pro Leu Thr Trp
```

```
1               5                   10                  15
Leu Ser Ser Pro Lys Thr Trp Thr Asn Val Thr Ser Tyr Ser Phe
                20                  25              30
Leu Ile Ser Leu Thr Ser Leu Thr Leu Leu Trp Gln Thr Asp Glu Asn
            35              40                  45
Tyr Lys Asn Phe Ser Asn Ile Phe Ser Ser Asp Pro Leu Ser Thr Pro
        50                  55              60
Leu Ile Ile Leu Thr Ala Trp Leu Leu Pro Leu Ile Leu Ile Ala Ser
65              70              75                  80
Gln Asn His Leu Lys Lys Asp Asn Asn Val Leu Gln Lys Leu Tyr Ile
                85              90              95
Ser Ile Leu Ile Ser Leu Gln Ile Leu Leu Ile Ile Thr Phe Ser Ala
            100             105             110
Thr Glu Leu Ile Ile Phe Tyr Ile Leu Phe Glu Ala Thr Leu Ile Pro
        115                 120                 125
Thr Leu Ile Ile Ile Thr Arg Trp Gly Asn Gln Thr Glu Arg Leu Asn
    130                 135                 140
Ala Gly Ile Tyr Phe Leu Phe Tyr Thr Leu Ile Gly Ser Ile Pro Leu
145                 150                 155                 160
Leu Ile Ala Leu Ile Leu Ile Gln Asn His Val Gly Thr Leu Asn Leu
            165                 170                 175
Ile Ile Leu Ser Phe Thr Thr His Thr Leu Asp Ala Ser Trp Ser Asn
            180                 185                 190
Asn Leu Leu Trp Leu Ala Cys Ile Ile Ala Phe Leu Ile Lys Ile Pro
        195                 200                 205
Leu Tyr Gly Val His Leu Trp Leu Pro Lys Ala His Val Glu Ala Pro
    210                 215                 220
Ile Ala Gly Ser Ile Ile Leu Ala Ala Ile Leu Leu Lys Leu Gly Ser
225                 230                 235                 240
Tyr Gly Ile Ile Arg Ile Ser Ile Ile Leu Asp Pro Leu Thr Lys Tyr
                245                 250                 255
Ile Ala Tyr Pro Phe Ile Leu Leu Ser Leu Trp Gly Ile Ile Ile Thr
            260                 265                 270
Ser Ser Ile Cys Leu Arg Gln Thr Asp Leu Lys Ser Leu Ile Ala Tyr
        275                 280                 285
Ser Ser Val Ser His Ile Ala Leu Val Ile Ala Ser Ile Ile Ile Gln
    290                 295                 300
Thr Pro Trp Ser Phe Ile Gly Ala Thr Ile Leu Ile Ile Ala His Gly
305                 310                 315                 320
Leu Thr Ser Ser Leu Leu Phe Cys Leu Ala Asn Ser Asn Tyr Glu Arg
                325                 330                 335
Ile His Ser Arg Thr Ile Met Ala Arg Gly Leu Gln Met Val Phe
            340                 345                 350
Pro Leu Ile Ala Thr Trp Trp Leu Ile Ala Ser Leu Ala Asn Leu Ala
            355                 360                 365
Leu Pro Pro Ser Ile Asn Leu Ile Gly Glu Leu Phe Ile Thr Ile Ser
        370                 375                 380
Leu Phe Ser Trp Ser Asn Phe Thr Ile Leu Ile Gly Ile Asn Ile
385                 390                 395                 400
Ile Ile Thr Gly Ile Tyr Ser Ile Tyr Ile Ile Thr Thr Gln Arg
                405                 410                 415
Gly Lys Leu Thr Asn His Ile Ile Asn Leu Gln Pro Ser His Thr Arg
            420                 425                 430
```

```
Glu Leu Thr Leu Ile Ala Leu His Ile Ile Pro Leu Ile Leu Leu Thr
        435                 440                 445

Thr Asn Pro Lys Leu Ile Thr Gly Leu Thr Ile Asp Tyr Lys Asp Asp
        450                 455                 460

Asp Asp Lys Met Val Phe Thr Leu Glu Asp Phe Val Gly Asp Trp Arg
465                 470                 475                 480

Gln Thr Ala Gly Tyr Asn Leu Asp Gln Val Leu Glu Gln Gly Gly Val
                    485                 490                 495

Ser Ser Leu Phe Gln Asn Leu Gly Val Ser Val Thr Pro Ile Gln
                500                 505                 510

<210> SEQ ID NO 7
<211> LENGTH: 2069
<212> TYPE: DNA
<213> ORGANISM: Artificial Sequence
<220> FEATURE:
<223> OTHER INFORMATION: Synthesized DNA enncoding a fusion protein
      consisting of ND4, FLAG tag and Luciferase
<220> FEATURE:
<221> NAME/KEY: CDS
<222> LOCATION: (7)..(1923)

<400> SEQUENCE: 7
```

| | | | | | | | | | | | | | | | | |
|---|---|---|---|---|---|---|---|---|---|---|---|---|---|---|---|---|
| ctgcag atg cta aaa att att ctt ccc tca cta atg cta cta cca cta | | | | | | | | | | | | | | | | 48 |
| | Met | Leu | Lys | Ile | Ile | Leu | Pro | Ser | Leu | Met | Leu | Leu | Pro | Leu | | |
| | 1 | | | 5 | | | | | 10 | | | | | | | |
| acc tga cta tca agc cct aaa aaa acc tga aca aac gta acc tca tat | | | | | | | | | | | | | | | | 96 |
| Thr | Trp | Leu | Ser | Ser | Pro | Lys | Lys | Thr | Trp | Thr | Asn | Val | Thr | Ser | Tyr | |
| 15 | | | | 20 | | | | | 25 | | | | | 30 | | |
| agt ttt cta att agt tta acc agc cta aca ctt cta tga caa acc gac | | | | | | | | | | | | | | | | 144 |
| Ser | Phe | Leu | Ile | Ser | Leu | Thr | Ser | Leu | Thr | Leu | Leu | Trp | Gln | Thr | Asp | |
| | | | | 35 | | | | | 40 | | | | | 45 | | |
| gaa aat tat aaa aac ttt tca aat ata ttc tcc tca gac ccc cta tcc | | | | | | | | | | | | | | | | 192 |
| Glu | Asn | Tyr | Lys | Asn | Phe | Ser | Asn | Ile | Phe | Ser | Ser | Asp | Pro | Leu | Ser | |
| | | 50 | | | | | 55 | | | | | 60 | | | | |
| aca cca tta att att tta aca gcc tga tta ctg cca cta ata tta ata | | | | | | | | | | | | | | | | 240 |
| Thr | Pro | Leu | Ile | Ile | Leu | Thr | Ala | Trp | Leu | Leu | Pro | Leu | Ile | Leu | Ile | |
| | 65 | | | | | 70 | | | | | 75 | | | | | |
| gct agc caa aac cac cta aaa aaa gat aat aac gta cta caa aaa ctc | | | | | | | | | | | | | | | | 288 |
| Ala | Ser | Gln | Asn | His | Leu | Lys | Lys | Asp | Asn | Asn | Val | Leu | Gln | Lys | Leu | |
| 80 | | | | | 85 | | | | | 90 | | | | | | |
| tac atc tca ata cta atc agc tta caa att ctc cta atc ata acc ttt | | | | | | | | | | | | | | | | 336 |
| Tyr | Ile | Ser | Ile | Leu | Ile | Ser | Leu | Gln | Ile | Leu | Leu | Ile | Ile | Thr | Phe | |
| 95 | | | | 100 | | | | | 105 | | | | | 110 | | |
| tca gca act gaa cta att ata ttt tat att tta ttt gaa gca acc tta | | | | | | | | | | | | | | | | 384 |
| Ser | Ala | Thr | Glu | Leu | Ile | Ile | Phe | Tyr | Ile | Leu | Phe | Glu | Ala | Thr | Leu | |
| | | | | 115 | | | | | 120 | | | | | 125 | | |
| atc cca aca ctt att att att acc cga tga ggg aac caa act gaa cgc | | | | | | | | | | | | | | | | 432 |
| Ile | Pro | Thr | Leu | Ile | Ile | Ile | Thr | Arg | Trp | Gly | Asn | Gln | Thr | Glu | Arg | |
| | | 130 | | | | | 135 | | | | | 140 | | | | |
| cta aac gca ggg att tat ttc cta ttt tat acc cta atc ggt tct att | | | | | | | | | | | | | | | | 480 |
| Leu | Asn | Ala | Gly | Ile | Tyr | Phe | Leu | Phe | Tyr | Thr | Leu | Ile | Gly | Ser | Ile | |
| | 145 | | | | | 150 | | | | | 155 | | | | | |
| cca ctg cta att gcc ctc atc tta atc caa aac cat gta gga acc cta | | | | | | | | | | | | | | | | 528 |
| Pro | Leu | Leu | Ile | Ala | Leu | Ile | Leu | Ile | Gln | Asn | His | Val | Gly | Thr | Leu | |
| 160 | | | | | 165 | | | | | 170 | | | | | | |
| aac ctc ata att tta tca ttc aca aca cac acc tta gac gct tca tga | | | | | | | | | | | | | | | | 576 |
| Asn | Leu | Ile | Ile | Leu | Ser | Phe | Thr | Thr | His | Thr | Leu | Asp | Ala | Ser | Trp | |
| 175 | | | | 180 | | | | | 185 | | | | | 190 | | |
| tct aac aac tta cta tgg ttg gca tgc ata ata gca ttt ctt att aaa | | | | | | | | | | | | | | | | 624 |

```
Ser Asn Asn Leu Leu Trp Leu Ala Cys Ile Ile Ala Phe Leu Ile Lys
            195             200             205 ata cca tta tat gga gtt cac cta tga cta cca aaa gcc cat gtt gaa      672
Ile Pro Leu Tyr Gly Val His Leu Trp Leu Pro Lys Ala His Val Glu
        210             215             220 gct cca att gct ggg tca ata att cta gca gct att ctt cta aaa tta      720
Ala Pro Ile Ala Gly Ser Ile Ile Leu Ala Ala Ile Leu Leu Lys Leu
            225             230             235 ggt agt tac gga ata att cgc atc tcc att att cta gac cca cta aca      768
Gly Ser Tyr Gly Ile Ile Arg Ile Ser Ile Ile Leu Asp Pro Leu Thr
        240             245             250 aaa tat ata gca tac ccc ttc atc ctt ctc tcc cta tga gga ata att      816
Lys Tyr Ile Ala Tyr Pro Phe Ile Leu Leu Ser Leu Trp Gly Ile Ile
255             260             265             270 ata act agc tca atc tgc tta cgc caa aca gat tta aaa tca cta atc      864
Ile Thr Ser Ser Ile Cys Leu Arg Gln Thr Asp Leu Lys Ser Leu Ile
            275             280             285 gcc tac tcc tca gtt agc cac ata gca ctt gtt att gca tca atc ata      912
Ala Tyr Ser Ser Val Ser His Ile Ala Leu Val Ile Ala Ser Ile Ile
        290             295             300 atc caa act cca tga agc ttc ata gga gca aca ata cta ata atc gca      960
Ile Gln Thr Pro Trp Ser Phe Ile Gly Ala Thr Ile Leu Ile Ile Ala
            305             310             315 cat ggc ctc aca tca tca ctc cta ttc tgc cta gca aac tcc aac tac     1008
His Gly Leu Thr Ser Ser Leu Leu Phe Cys Leu Ala Asn Ser Asn Tyr
320             325             330 gaa cgg atc cac agc cgt act ata atc atg gcc cga gga ctt caa atg     1056
Glu Arg Ile His Ser Arg Thr Ile Ile Met Ala Arg Gly Leu Gln Met
335             340             345             350 gtc ttc cca ctt ata gcc aca tga tga ctg ata gca agt cta gct aat     1104
Val Phe Pro Leu Ile Ala Thr Trp Trp Leu Ile Ala Ser Leu Ala Asn
        355             360             365 cta gct cta ccc cct tca atc aat cta ata gga gaa tta ttc att acc     1152
Leu Ala Leu Pro Pro Ser Ile Asn Leu Ile Gly Glu Leu Phe Ile Thr
        370             375             380 ata tca tta ttt tct tga tca aac ttt acc att att ctt ata gga att     1200
Ile Ser Leu Phe Ser Trp Ser Asn Phe Thr Ile Ile Leu Ile Gly Ile
            385             390             395 aac att att att aca ggt ata tac tca ata tac ata att acc acc         1248
Asn Ile Ile Ile Thr Gly Ile Tyr Ser Ile Tyr Ile Ile Thr Thr
400             405             410 caa cgc ggc aaa cta acc aac cat ata att aac ctc caa ccc tca cac     1296
Gln Arg Gly Lys Leu Thr Asn His Ile Ile Asn Leu Gln Pro Ser His
415             420             425             430 aca cga gaa cta aca cta ata gcc ctt cac ata att cca ctt att ctt     1344
Thr Arg Glu Leu Thr Leu Ile Ala Leu His Ile Ile Pro Leu Ile Leu
        435             440             445 cta act acc aat cca aaa cta att aca ggc tgg aca ata gat tac aag     1392
Leu Thr Thr Asn Pro Lys Leu Ile Thr Gly Leu Thr Ile Asp Tyr Lys
        450             455             460 gat gac gac gat aag atg gtc ttc aca ctc gaa gat ttc gtt ggg gac     1440
Asp Asp Asp Asp Lys Met Val Phe Thr Leu Glu Asp Phe Val Gly Asp
            465             470             475 tga cga cag aca gcc ggc tac aac ctg gac caa gtc ctt gaa cag gga     1488
Trp Arg Gln Thr Ala Gly Tyr Asn Leu Asp Gln Val Leu Glu Gln Gly
        480             485             490 ggt gtg tcc agt ttg ttt cag aat ctc ggg gtg tcc gta act ccg atc     1536
Gly Val Ser Ser Leu Phe Gln Asn Leu Gly Val Ser Val Thr Pro Ile
495             500             505             510
```

```
caa cgg att gtc ctg agc ggt gaa aat ggg ctg aag atc gac atc cat    1584
Gln Arg Ile Val Leu Ser Gly Glu Asn Gly Leu Lys Ile Asp Ile His
            515                 520                 525 gtc atc atc ccg tat gaa ggt ctg agc ggc gac caa atg ggc cag atc    1632
Val Ile Ile Pro Tyr Glu Gly Leu Ser Gly Asp Gln Met Gly Gln Ile
        530                 535                 540 gaa aaa att ttt aag gtg gtg tac cct gtg gat gat cat cac ttt aag    1680
Glu Lys Ile Phe Lys Val Val Tyr Pro Val Asp Asp His His Phe Lys
    545                 550                 555 gtg atc ctg cac tat ggc aca ctg gta atc gac ggg gtt acg ccg aac    1728
Val Ile Leu His Tyr Gly Thr Leu Val Ile Asp Gly Val Thr Pro Asn
560                 565                 570 atg atc gac tat ttc gga cgg ccg tat gaa ggc atc gcc gtg ttc gac    1776
Met Ile Asp Tyr Phe Gly Arg Pro Tyr Glu Gly Ile Ala Val Phe Asp
575                 580                 585                 590 ggc aaa aag atc act gta aca ggg acc ctg tgg aac ggc aac aaa att    1824
Gly Lys Lys Ile Thr Val Thr Gly Thr Leu Trp Asn Gly Asn Lys Ile
            595                 600                 605 atc gac gag cgc ctg atc aac ccc gac ggc tcc ctg ctg ttc cga gta    1872
Ile Asp Glu Arg Leu Ile Asn Pro Asp Gly Ser Leu Leu Phe Arg Val
        610                 615                 620 acc atc aac gga gtg acc ggc tgg cgg ctg tgc gaa cgc att ctg gcg    1920
Thr Ile Asn Gly Val Thr Gly Trp Arg Leu Cys Glu Arg Ile Leu Ala
    625                 630                 635 taa gaaaggaagg aatcgaaccc cctaaaattg gtttcaagcc aatctcatat         1973
cctatatgtc tttctcaata agatattagt aaaatcaatt acataacttt gtcaaagtta  2033
aattatagat caataatcta tatatcttat ctgcag                            2069

<210> SEQ ID NO 8
<211> LENGTH: 638
<212> TYPE: PRT
<213> ORGANISM: Artificial Sequence
<220> FEATURE:
<223> OTHER INFORMATION: Synthetic Construct

<400> SEQUENCE: 8

Met Leu Lys Ile Ile Leu Pro Ser Leu Met Leu Leu Pro Leu Thr Trp
1               5                   10                  15

Leu Ser Ser Pro Lys Lys Thr Trp Thr Asn Val Thr Ser Tyr Ser Phe
            20                  25                  30

Leu Ile Ser Leu Thr Ser Leu Thr Leu Leu Trp Gln Thr Asp Glu Asn
        35                  40                  45

Tyr Lys Asn Phe Ser Asn Ile Phe Ser Ser Asp Pro Leu Ser Thr Pro
    50                  55                  60

Leu Ile Ile Leu Thr Ala Trp Leu Leu Pro Leu Ile Leu Ile Ala Ser
65                  70                  75                  80

Gln Asn His Leu Lys Lys Asp Asn Asn Val Leu Gln Lys Leu Tyr Ile
                85                  90                  95

Ser Ile Leu Ile Ser Leu Gln Ile Leu Leu Ile Ile Thr Phe Ser Ala
            100                 105                 110

Thr Glu Leu Ile Ile Phe Tyr Ile Leu Phe Glu Ala Thr Leu Ile Pro
        115                 120                 125

Thr Leu Ile Ile Ile Thr Arg Trp Gly Asn Gln Thr Glu Arg Leu Asn
    130                 135                 140

Ala Gly Ile Tyr Phe Leu Phe Tyr Thr Leu Ile Gly Ser Ile Pro Leu
145                 150                 155                 160

Leu Ile Ala Leu Ile Leu Ile Gln Asn His Val Gly Thr Leu Asn Leu
```

165                 170                 175
Ile Ile Leu Ser Phe Thr Thr His Thr Leu Asp Ala Ser Trp Ser Asn
                180                 185                 190

Asn Leu Leu Trp Leu Ala Cys Ile Ile Ala Phe Leu Ile Lys Ile Pro
        195                 200                 205

Leu Tyr Gly Val His Leu Trp Leu Pro Lys Ala His Val Glu Ala Pro
210                 215                 220

Ile Ala Gly Ser Ile Ile Leu Ala Ala Ile Leu Leu Lys Leu Gly Ser
225                 230                 235                 240

Tyr Gly Ile Ile Arg Ile Ser Ile Ile Leu Asp Pro Leu Thr Lys Tyr
            245                 250                 255

Ile Ala Tyr Pro Phe Ile Leu Leu Ser Leu Trp Gly Ile Ile Ile Thr
                260                 265                 270

Ser Ser Ile Cys Leu Arg Gln Thr Asp Leu Lys Ser Leu Ile Ala Tyr
        275                 280                 285

Ser Ser Val Ser His Ile Ala Leu Val Ile Ala Ser Ile Ile Ile Gln
290                 295                 300

Thr Pro Trp Ser Phe Ile Gly Ala Thr Ile Leu Ile Ile Ala His Gly
305                 310                 315                 320

Leu Thr Ser Ser Leu Leu Phe Cys Leu Ala Asn Ser Asn Tyr Glu Arg
            325                 330                 335

Ile His Ser Arg Thr Ile Ile Met Ala Arg Gly Leu Gln Met Val Phe
                340                 345                 350

Pro Leu Ile Ala Thr Trp Trp Leu Ile Ala Ser Leu Ala Asn Leu Ala
            355                 360                 365

Leu Pro Pro Ser Ile Asn Leu Ile Gly Glu Leu Phe Ile Thr Ile Ser
370                 375                 380

Leu Phe Ser Trp Ser Asn Phe Thr Ile Ile Leu Ile Gly Ile Asn Ile
385                 390                 395                 400

Ile Ile Thr Gly Ile Tyr Ser Ile Tyr Ile Ile Thr Thr Gln Arg
                405                 410                 415

Gly Lys Leu Thr Asn His Ile Ile Asn Leu Gln Pro Ser His Thr Arg
            420                 425                 430

Glu Leu Thr Leu Ile Ala Leu His Ile Ile Pro Leu Ile Leu Leu Thr
        435                 440                 445

Thr Asn Pro Lys Leu Ile Thr Gly Leu Thr Ile Asp Tyr Lys Asp Asp
    450                 455                 460

Asp Asp Lys Met Val Phe Thr Leu Glu Asp Phe Val Gly Asp Trp Arg
465                 470                 475                 480

Gln Thr Ala Gly Tyr Asn Leu Asp Gln Val Leu Glu Gln Gly Gly Val
                485                 490                 495

Ser Ser Leu Phe Gln Asn Leu Gly Val Ser Val Thr Pro Ile Gln Arg
            500                 505                 510

Ile Val Leu Ser Gly Glu Asn Gly Leu Lys Ile Asp Ile His Val Ile
        515                 520                 525

Ile Pro Tyr Glu Gly Leu Ser Gly Asp Gln Met Gly Gln Ile Glu Lys
    530                 535                 540

Ile Phe Lys Val Val Tyr Pro Val Asp Asp His His Phe Lys Val Ile
545                 550                 555                 560

Leu His Tyr Gly Thr Leu Val Ile Asp Gly Val Thr Pro Asn Met Ile
                565                 570                 575

Asp Tyr Phe Gly Arg Pro Tyr Glu Gly Ile Ala Val Phe Asp Gly Lys
            580                 585                 590

```
Lys Ile Thr Val Thr Gly Thr Leu Trp Asn Gly Asn Lys Ile Ile Asp
        595                 600                 605

Glu Arg Leu Ile Asn Pro Asp Gly Ser Leu Leu Phe Arg Val Thr Ile
        610                 615                 620

Asn Gly Val Thr Gly Trp Arg Leu Cys Glu Arg Ile Leu Ala
625                 630                 635

<210> SEQ ID NO 9
<211> LENGTH: 2267
<212> TYPE: DNA
<213> ORGANISM: Artificial Sequence
<220> FEATURE:
<223> OTHER INFORMATION: Synthesized DNA encoding a fusion protein
      consisting of ND4, FLAG tag and Luciferase
<220> FEATURE:
<221> NAME/KEY: CDS
<222> LOCATION: (205)..(2121)

<400> SEQUENCE: 9
ctgcagccct cctcttaatg ccaaacccca aaaacactaa gaacttgaaa gacatataat        60
attaactatc aaaccctatg tcctgatcaa ttctagtagt tcccaaaata tgacttatat       120
tttagtactt gtaaaaattt tacaaaatca tgttccgtga accaaaactc taatcatact       180
ctattacgca ataacatta acaa atg cta aaa att att ctt ccc tca cta           231
                          Met Leu Lys Ile Ile Leu Pro Ser Leu
                            1               5 atg cta cta cca cta acc tga cta tca agc cct aaa aaa acc tga aca         279
Met Leu Leu Pro Leu Thr Trp Leu Ser Ser Pro Lys Lys Thr Trp Thr
 10                  15                  20                  25 aac gta acc tca tat agt ttt cta att agt tta acc agc cta aca ctt         327
Asn Val Thr Ser Tyr Ser Phe Leu Ile Ser Leu Thr Ser Leu Thr Leu
                 30                  35                  40 cta tga caa acc gac gaa aat tat aaa aac ttt tca aat ata ttc tcc         375
Leu Trp Gln Thr Asp Glu Asn Tyr Lys Asn Phe Ser Asn Ile Phe Ser
             45                  50                  55 tca gac ccc cta tcc aca cca tta att att tta aca gcc tga tta ctg         423
Ser Asp Pro Leu Ser Thr Pro Leu Ile Ile Leu Thr Ala Trp Leu Leu
         60                  65                  70 cca cta ata tta ata gct agc caa aac cac cta aaa aaa gat aat aac         471
Pro Leu Ile Leu Ile Ala Ser Gln Asn His Leu Lys Lys Asp Asn Asn
 75                  80                  85 gta cta caa aaa ctc tac atc tca ata cta atc agc tta caa att ctc         519
Val Leu Gln Lys Leu Tyr Ile Ser Ile Leu Ile Ser Leu Gln Ile Leu
 90                  95                 100                 105 cta atc ata acc ttt tca gca act gaa cta att ata ttt tat att tta         567
Leu Ile Ile Thr Phe Ser Ala Thr Glu Leu Ile Ile Phe Tyr Ile Leu
                110                 115                 120 ttt gaa gca acc tta atc cca aca ctt att att att acc cga tga ggg         615
Phe Glu Ala Thr Leu Ile Pro Thr Leu Ile Ile Ile Thr Arg Trp Gly
             125                 130                 135 aac caa act gaa cgc cta aac gca ggg att tat ttc cta ttt tat acc         663
Asn Gln Thr Glu Arg Leu Asn Ala Gly Ile Tyr Phe Leu Phe Tyr Thr
         140                 145                 150 cta atc ggt tct att cca ctg cta att gcc ctc atc tta atc caa aac         711
Leu Ile Gly Ser Ile Pro Leu Leu Ile Ala Leu Ile Leu Ile Gln Asn
 155                 160                 165 cat gta gga acc cta aac ctc ata att tta tca ttc aca aca cac acc         759
His Val Gly Thr Leu Asn Leu Ile Ile Leu Ser Phe Thr Thr His Thr
170                 175                 180                 185 tta gac gct tca tga tct aac aac tta cta tgg ttg gca tgc ata ata         807
```

```
Leu Asp Ala Ser Trp Ser Asn Asn Leu Leu Trp Leu Ala Cys Ile Ile
            190                 195                 200 gca ttt ctt att aaa ata cca tta tat gga gtt cac cta tga cta cca        855
Ala Phe Leu Ile Lys Ile Pro Leu Tyr Gly Val His Leu Trp Leu Pro
            205                 210                 215 aaa gcc cat gtt gaa gct cca att gct ggg tca ata att cta gca gct        903
Lys Ala His Val Glu Ala Pro Ile Ala Gly Ser Ile Ile Leu Ala Ala
            220                 225                 230 att ctt cta aaa tta ggt agt tac gga ata att cgc atc tcc att att        951
Ile Leu Leu Lys Leu Gly Ser Tyr Gly Ile Ile Arg Ile Ser Ile Ile
            235                 240                 245 cta gac cca cta aca aaa tat ata gca tac ccc ttc atc ctt ctc tcc        999
Leu Asp Pro Leu Thr Lys Tyr Ile Ala Tyr Pro Phe Ile Leu Leu Ser
250                 255                 260                 265 cta tga gga ata att ata act agc tca atc tgc tta cgc caa aca gat       1047
Leu Trp Gly Ile Ile Ile Thr Ser Ser Ile Cys Leu Arg Gln Thr Asp
                    270                 275                 280 tta aaa tca cta atc gcc tac tcc tca gtt agc cac ata gca ctt gtt       1095
Leu Lys Ser Leu Ile Ala Tyr Ser Ser Val Ser His Ile Ala Leu Val
                285                 290                 295 att gca tca atc ata atc caa act cca tga agc ttc ata gga gca aca       1143
Ile Ala Ser Ile Ile Ile Gln Thr Pro Trp Ser Phe Ile Gly Ala Thr
            300                 305                 310 ata cta ata atc gca cat ggc ctc aca tca tca ctc cta ttc tgc cta       1191
Ile Leu Ile Ile Ala His Gly Leu Thr Ser Ser Leu Leu Phe Cys Leu
            315                 320                 325 gca aac tcc aac tac gaa cgg atc cac agc cgt act ata atc atg gcc       1239
Ala Asn Ser Asn Tyr Glu Arg Ile His Ser Arg Thr Ile Ile Met Ala
330                 335                 340                 345 cga gga ctt caa atg gtc ttc cca ctt ata gcc aca tga tga ctg ata       1287
Arg Gly Leu Gln Met Val Phe Pro Leu Ile Ala Thr Trp Trp Leu Ile
                    350                 355                 360 gca agt cta gct aat cta gct cta ccc cct tca atc aat cta ata gga       1335
Ala Ser Leu Ala Asn Leu Ala Leu Pro Pro Ser Ile Asn Leu Ile Gly
                365                 370                 375 gaa tta ttc att acc ata tca tta ttt tct tga tca aac ttt acc att       1383
Glu Leu Phe Ile Thr Ile Ser Leu Phe Ser Trp Ser Asn Phe Thr Ile
            380                 385                 390 att ctt ata gga att aac att att att aca ggt ata tac tca ata tac       1431
Ile Leu Ile Gly Ile Asn Ile Ile Ile Thr Gly Ile Tyr Ser Ile Tyr
            395                 400                 405 ata att att acc acc caa cgc ggc aaa cta acc aac cat ata att aac       1479
Ile Ile Ile Thr Thr Gln Arg Gly Lys Leu Thr Asn His Ile Ile Asn
410                 415                 420                 425 ctc caa ccc tca cac aca cga gaa cta aca cta ata gcc ctt cac ata       1527
Leu Gln Pro Ser His Thr Arg Glu Leu Thr Leu Ile Ala Leu His Ile
                    430                 435                 440 att cca ctt att ctt cta act acc aat cca aaa cta att aca ggc ctg       1575
Ile Pro Leu Ile Leu Leu Thr Thr Asn Pro Lys Leu Ile Thr Gly Leu
                445                 450                 455 aca ata gat tac aag gat gac gac gat aag atg gtc ttc aca ctc gaa       1623
Thr Ile Asp Tyr Lys Asp Asp Asp Lys Met Val Phe Thr Leu Glu
            460                 465                 470 gat ttc gtt ggg gac tga cga cag aca gcc ggc tac aac ctg gac caa       1671
Asp Phe Val Gly Asp Trp Arg Gln Thr Ala Gly Tyr Asn Leu Asp Gln
            475                 480                 485 gtc ctt gaa cag gga ggt gtg tcc agt ttg ttt cag aat ctc ggg gtg       1719
Val Leu Glu Gln Gly Gly Val Ser Ser Leu Phe Gln Asn Leu Gly Val
490                 495                 500                 505
```

```
tcc gta act ccg atc caa cgg att gtc ctg agc ggt gaa aat ggg ctg      1767
Ser Val Thr Pro Ile Gln Arg Ile Val Leu Ser Gly Glu Asn Gly Leu
                510                 515                 520 aag atc gac atc cat gtc atc atc ccg tat gaa ggt ctg agc ggc gac      1815
Lys Ile Asp Ile His Val Ile Ile Pro Tyr Glu Gly Leu Ser Gly Asp
                525                 530                 535 caa atg ggc cag atc gaa aaa att ttt aag gtg gtg tac cct gtg gat      1863
Gln Met Gly Gln Ile Glu Lys Ile Phe Lys Val Val Tyr Pro Val Asp
                540                 545                 550 gat cat cac ttt aag gtg atc ctg cac tat ggc aca ctg gta atc gac      1911
Asp His His Phe Lys Val Ile Leu His Tyr Gly Thr Leu Val Ile Asp
            555                 560                 565 ggg gtt acg ccg aac atg atc gac tat ttc gga cgg ccg tat gaa ggc      1959
Gly Val Thr Pro Asn Met Ile Asp Tyr Phe Gly Arg Pro Tyr Glu Gly
570                 575                 580                 585 atc gcc gtg ttc gac ggc aaa aag atc act gta aca ggg acc ctg tgg      2007
Ile Ala Val Phe Asp Gly Lys Lys Ile Thr Val Thr Gly Thr Leu Trp
                590                 595                 600 aac ggc aac aaa att atc gac gag cgc ctg atc aac ccc gac ggc tcc      2055
Asn Gly Asn Lys Ile Ile Asp Glu Arg Leu Ile Asn Pro Asp Gly Ser
                605                 610                 615 ctg ctg ttc cga gta acc atc aac gga gtg acc ggc tgg cgg ctg tgc      2103
Leu Leu Phe Arg Val Thr Ile Asn Gly Val Thr Gly Trp Arg Leu Cys
                620                 625                 630 gaa cgc att ctg gcg taa gaaaggaagg aatcgaaccc cctaaaattg             2151
Glu Arg Ile Leu Ala
                635 gtttcaagcc aatctcatat cctatatgtc tttctcaata agatattagt aaaatcaatt   2211 acataacttt gtcaaagtta aattatagat caataatcta tatatcttat ctgcag       2267

<210> SEQ ID NO 10
<211> LENGTH: 638
<212> TYPE: PRT
<213> ORGANISM: Artificial Sequence
<220> FEATURE:
<223> OTHER INFORMATION: Synthetic Construct

<400> SEQUENCE: 10

Met Leu Lys Ile Ile Leu Pro Ser Leu Met Leu Leu Pro Leu Thr Trp
1               5                   10                  15

Leu Ser Ser Pro Lys Lys Thr Trp Thr Asn Val Thr Ser Tyr Ser Phe
            20                  25                  30

Leu Ile Ser Leu Thr Ser Leu Thr Leu Leu Trp Gln Thr Asp Glu Asn
        35                  40                  45

Tyr Lys Asn Phe Ser Asn Ile Phe Ser Ser Asp Pro Leu Ser Thr Pro
    50                  55                  60

Leu Ile Ile Leu Thr Ala Trp Leu Leu Pro Leu Ile Leu Ile Ala Ser
65                  70                  75                  80

Gln Asn His Leu Lys Lys Asp Asn Asn Val Leu Gln Lys Leu Tyr Ile
                85                  90                  95

Ser Ile Leu Ile Ser Leu Gln Ile Leu Leu Ile Ile Thr Phe Ser Ala
            100                 105                 110

Thr Glu Leu Ile Ile Phe Tyr Ile Leu Phe Glu Ala Thr Leu Ile Pro
        115                 120                 125

Thr Leu Ile Ile Ile Thr Arg Trp Gly Asn Gln Thr Glu Arg Leu Asn
    130                 135                 140

Ala Gly Ile Tyr Phe Leu Phe Tyr Thr Leu Ile Gly Ser Ile Pro Leu
145                 150                 155                 160
```

```
Leu Ile Ala Leu Ile Leu Ile Gln Asn His Val Gly Thr Leu Asn Leu
                165                 170                 175

Ile Ile Leu Ser Phe Thr Thr His Thr Leu Asp Ala Ser Trp Ser Asn
            180                 185                 190

Asn Leu Leu Trp Leu Ala Cys Ile Ile Ala Phe Leu Ile Lys Ile Pro
        195                 200                 205

Leu Tyr Gly Val His Leu Trp Leu Pro Lys Ala His Val Glu Ala Pro
    210                 215                 220

Ile Ala Gly Ser Ile Ile Leu Ala Ala Ile Leu Leu Lys Leu Gly Ser
225                 230                 235                 240

Tyr Gly Ile Ile Arg Ile Ser Ile Ile Leu Asp Pro Leu Thr Lys Tyr
                245                 250                 255

Ile Ala Tyr Pro Phe Ile Leu Leu Ser Leu Trp Gly Ile Ile Ile Thr
            260                 265                 270

Ser Ser Ile Cys Leu Arg Gln Thr Asp Leu Lys Ser Leu Ile Ala Tyr
        275                 280                 285

Ser Ser Val Ser His Ile Ala Leu Val Ile Ala Ser Ile Ile Ile Gln
    290                 295                 300

Thr Pro Trp Ser Phe Ile Gly Ala Thr Ile Leu Ile Ile Ala His Gly
305                 310                 315                 320

Leu Thr Ser Ser Leu Leu Phe Cys Leu Ala Asn Ser Asn Tyr Glu Arg
                325                 330                 335

Ile His Ser Arg Thr Ile Ile Met Ala Arg Gly Leu Gln Met Val Phe
            340                 345                 350

Pro Leu Ile Ala Thr Trp Trp Leu Ile Ala Ser Leu Ala Asn Leu Ala
        355                 360                 365

Leu Pro Pro Ser Ile Asn Leu Ile Gly Glu Leu Phe Ile Thr Ile Ser
    370                 375                 380

Leu Phe Ser Trp Ser Asn Phe Thr Ile Leu Ile Gly Ile Asn Ile
385                 390                 395                 400

Ile Ile Thr Gly Ile Tyr Ser Ile Tyr Ile Ile Thr Thr Gln Arg
                405                 410                 415

Gly Lys Leu Thr Asn His Ile Ile Asn Leu Gln Pro Ser His Thr Arg
            420                 425                 430

Glu Leu Thr Leu Ile Ala Leu His Ile Ile Pro Leu Ile Leu Leu Thr
        435                 440                 445

Thr Asn Pro Lys Leu Ile Thr Gly Leu Thr Ile Asp Tyr Lys Asp Asp
    450                 455                 460

Asp Asp Lys Met Val Phe Thr Leu Glu Asp Phe Val Gly Asp Trp Arg
465                 470                 475                 480

Gln Thr Ala Gly Tyr Asn Leu Asp Gln Val Leu Glu Gln Gly Gly Val
                485                 490                 495

Ser Ser Leu Phe Gln Asn Leu Gly Val Ser Val Thr Pro Ile Gln Arg
            500                 505                 510

Ile Val Leu Ser Gly Glu Asn Gly Leu Lys Ile Asp Ile His Val Ile
        515                 520                 525

Ile Pro Tyr Glu Gly Leu Ser Gly Asp Gln Met Gly Gln Ile Glu Lys
    530                 535                 540

Ile Phe Lys Val Val Tyr Pro Val Asp Asp His His Phe Lys Val Ile
545                 550                 555                 560

Leu His Tyr Gly Thr Leu Val Ile Asp Gly Val Thr Pro Asn Met Ile
                565                 570                 575
```

```
Asp Tyr Phe Gly Arg Pro Tyr Glu Gly Ile Ala Val Phe Asp Gly Lys
            580                 585                 590

Lys Ile Thr Val Thr Gly Thr Leu Trp Asn Gly Asn Lys Ile Ile Asp
        595                 600                 605

Glu Arg Leu Ile Asn Pro Asp Gly Ser Leu Leu Phe Arg Val Thr Ile
        610                 615                 620

Asn Gly Val Thr Gly Trp Arg Leu Cys Glu Arg Ile Leu Ala
625                 630                 635

<210> SEQ ID NO 11
<211> LENGTH: 2267
<212> TYPE: DNA
<213> ORGANISM: Artificial Sequence
<220> FEATURE:
<223> OTHER INFORMATION: Synthesized DNA encoding a fusion protein
      consisting of ND4, FLAG tag and Luciferase
<220> FEATURE:
<221> NAME/KEY: CDS
<222> LOCATION: (205)..(1740)

<400> SEQUENCE: 11
ctgcagccct cctcttaatg ccaaacccca aaaacactaa gaacttgaaa gacatataat      60
attaactatc aaaccctatg tcctgatcaa ttctagtagt tcccaaaata tgacttatat     120
tttagtactt gtaaaaattt tacaaaatca tgttccgtga accaaaactc taatcatact     180
ctattacgca ataaacatta acaa atg cta aaa att att ctt ccc tca cta        231
                           Met Leu Lys Ile Ile Leu Pro Ser Leu
                                 1               5 atg cta cta cca cta acc tga cta tca agc cct aaa aaa acc tga aca       279
Met Leu Leu Pro Leu Thr Trp Leu Ser Ser Pro Lys Lys Thr Trp Thr
 10                  15                  20                  25 aac gta acc tca tat agt ttt cta att agt tta acc agc cta aca ctt       327
Asn Val Thr Ser Tyr Ser Phe Leu Ile Ser Leu Thr Ser Leu Thr Leu
                 30                  35                  40 cta tga caa acc gac gaa aat tat aaa aac ttt tca aat ata ttc tcc       375
Leu Trp Gln Thr Asp Glu Asn Tyr Lys Asn Phe Ser Asn Ile Phe Ser
             45                  50                  55 tca gac ccc cta tcc aca cca tta att att tta aca gcc tga tta ctg       423
Ser Asp Pro Leu Ser Thr Pro Leu Ile Ile Leu Thr Ala Trp Leu Leu
         60                  65                  70 cca cta ata tta ata gct agc caa aac cac cta aaa aaa gat aat aac       471
Pro Leu Ile Leu Ile Ala Ser Gln Asn His Leu Lys Lys Asp Asn Asn
     75                  80                  85 gta cta caa aaa ctc tac atc tca ata cta atc agc tta caa att ctc       519
Val Leu Gln Lys Leu Tyr Ile Ser Ile Leu Ile Ser Leu Gln Ile Leu
 90                  95                 100                 105 cta atc ata acc ttt tca gca act gaa cta att ata ttt tat att tta       567
Leu Ile Ile Thr Phe Ser Ala Thr Glu Leu Ile Ile Phe Tyr Ile Leu
                110                 115                 120 ttt gaa gca acc tta atc cca aca ctt att att att acc cga tga ggg       615
Phe Glu Ala Thr Leu Ile Pro Thr Leu Ile Ile Ile Thr Arg Trp Gly
            125                 130                 135 aac caa act gaa cgc cta aac gca ggg att tat ttc cta ttt tat acc       663
Asn Gln Thr Glu Arg Leu Asn Ala Gly Ile Tyr Phe Leu Phe Tyr Thr
        140                 145                 150 cta atc ggt tct att cca ctg cta att gcc ctc atc tta atc caa aac       711
Leu Ile Gly Ser Ile Pro Leu Leu Ile Ala Leu Ile Leu Ile Gln Asn
    155                 160                 165 cat gta gga acc cta aac ctc ata att tta tca ttc aca aca cac acc       759
His Val Gly Thr Leu Asn Leu Ile Ile Leu Ser Phe Thr Thr His Thr
170                 175                 180                 185
```

```
tta gac gct tca tga tct aac aac tta cta tgg ttg gca tgc ata ata          807
Leu Asp Ala Ser Trp Ser Asn Asn Leu Leu Trp Leu Ala Cys Ile Ile
            190                 195                 200 gca ttt ctt att aaa ata cca tta tat gga gtt cac cta tga cta cca          855
Ala Phe Leu Ile Lys Ile Pro Leu Tyr Gly Val His Leu Trp Leu Pro
                205                 210                 215 aaa gcc cat gtt gaa gct cca att gct ggg tca ata att cta gca gct          903
Lys Ala His Val Glu Ala Pro Ile Ala Gly Ser Ile Ile Leu Ala Ala
            220                 225                 230 att ctt cta aaa tta ggt agt tac gga ata att cgc atc tcc att att          951
Ile Leu Leu Lys Leu Gly Ser Tyr Gly Ile Ile Arg Ile Ser Ile Ile
            235                 240                 245 cta gac cca cta aca aaa tat ata gca tac ccc ttc atc ctt ctc tcc          999
Leu Asp Pro Leu Thr Lys Tyr Ile Ala Tyr Pro Phe Ile Leu Leu Ser
250                 255                 260                 265 cta tga gga ata att ata act agc tca atc tgc tta cgc caa aca gat         1047
Leu Trp Gly Ile Ile Ile Thr Ser Ser Ile Cys Leu Arg Gln Thr Asp
                270                 275                 280 tta aaa tca cta atc gcc tac tcc tca gtt agc cac ata gca ctt gtt         1095
Leu Lys Ser Leu Ile Ala Tyr Ser Ser Val Ser His Ile Ala Leu Val
            285                 290                 295 att gca tca atc ata atc caa act cca tga agc ttc ata gga gca aca         1143
Ile Ala Ser Ile Ile Ile Gln Thr Pro Trp Ser Phe Ile Gly Ala Thr
            300                 305                 310 ata cta ata atc gca cat ggc ctc aca tca tca ctc cta ttc tgc cta         1191
Ile Leu Ile Ile Ala His Gly Leu Thr Ser Ser Leu Leu Phe Cys Leu
            315                 320                 325 gca aac tcc aac tac gaa cgg atc cac agc cgt act ata atc atg gcc         1239
Ala Asn Ser Asn Tyr Glu Arg Ile His Ser Arg Thr Ile Ile Met Ala
330                 335                 340                 345 cga gga ctt caa atg gtc ttc cca ctt ata gcc aca tga tga ctg ata         1287
Arg Gly Leu Gln Met Val Phe Pro Leu Ile Ala Thr Trp Trp Leu Ile
                350                 355                 360 gca agt cta gct aat cta gct cta ccc cct tca atc aat cta ata gga         1335
Ala Ser Leu Ala Asn Leu Ala Leu Pro Pro Ser Ile Asn Leu Ile Gly
            365                 370                 375 gaa tta ttc att acc ata tca tta ttt tct tga tca aac ttt acc att         1383
Glu Leu Phe Ile Thr Ile Ser Leu Phe Ser Trp Ser Asn Phe Thr Ile
            380                 385                 390 att ctt ata gga att aac att att att aca ggt ata tac tca ata tac         1431
Ile Leu Ile Gly Ile Asn Ile Ile Ile Thr Gly Ile Tyr Ser Ile Tyr
            395                 400                 405 ata att att acc acc caa cgc ggc aaa cta acc aac cat ata att aac         1479
Ile Ile Ile Thr Thr Gln Arg Gly Lys Leu Thr Asn His Ile Ile Asn
410                 415                 420                 425 ctc caa ccc tca cac aca cga gaa cta aca cta ata gcc ctt cac ata         1527
Leu Gln Pro Ser His Thr Arg Glu Leu Thr Leu Ile Ala Leu His Ile
            430                 435                 440 att cca ctt att ctt cta act acc aat cca aaa cta att aca ggc ctg         1575
Ile Pro Leu Ile Leu Leu Thr Thr Asn Pro Lys Leu Ile Thr Gly Leu
            445                 450                 455 aca ata gat tac aag gat gac gac gat aag atg gtc ttc aca ctc gaa         1623
Thr Ile Asp Tyr Lys Asp Asp Asp Lys Met Val Phe Thr Leu Glu
            460                 465                 470 gat ttc gtt ggg gac tga cga cag aca gcc ggc tac aac ctg gac caa         1671
Asp Phe Val Gly Asp Trp Arg Gln Thr Ala Gly Tyr Asn Leu Asp Gln
            475                 480                 485 gtc ctt gaa cag gga ggt gtg tcc agt ttg ttt cag aat ctc ggg gtg         1719
Val Leu Glu Gln Gly Gly Val Ser Ser Leu Phe Gln Asn Leu Gly Val
```

```
                490         495         500         505
tcc gta act ccg atc caa tag attgtcctga gcggtgaaaa tgggctgaag    1770
Ser Val Thr Pro Ile Gln
                510 atcgacatcc atgtcatcat cccgtatgaa ggtctgagcg cgaccaaat gggccagatc  1830 gaaaaatttt ttaaggtggt gtaccctgtg gatgatcatc actttaaggt gatcctgcac  1890 tatggcacac tggtaatcga cggggttacg ccgaacatga tcgactattt cggacggccg  1950 tatgaaggca tcgccgtgtt cgacggcaaa aagatcactg taacagggac cctgtggaac  2010 ggcaacaaaa ttatcgacga gcgcctgatc aaccccgacg gctccctgct gttccgagta  2070 accatcaacg gagtgaccgg ctggcggctg tgcgaacgca ttctggcgta agaaaggaag  2130 gaatcgaacc ccctaaaatt ggtttcaagc caatctcata tcctatatgt ctttctcaat  2190 aagatattag taaaatcaat tacataactt tgtcaaagtt aaattataga tcaataatct  2250 atatatctta tctgcag                                                2267
```

<210> SEQ ID NO 12
<211> LENGTH: 511
<212> TYPE: PRT
<213> ORGANISM: Artificial Sequence
<220> FEATURE:
<223> OTHER INFORMATION: Synthetic Construct

<400> SEQUENCE: 12

```
Met Leu Lys Ile Ile Leu Pro Ser Leu Met Leu Leu Pro Leu Thr Trp
1               5                   10                  15

Leu Ser Ser Pro Lys Lys Thr Trp Thr Asn Val Thr Ser Tyr Ser Phe
            20                  25                  30

Leu Ile Ser Leu Thr Ser Leu Thr Leu Leu Trp Gln Thr Asp Glu Asn
        35                  40                  45

Tyr Lys Asn Phe Ser Asn Ile Phe Ser Ser Asp Pro Leu Ser Thr Pro
    50                  55                  60

Leu Ile Ile Leu Thr Ala Trp Leu Leu Pro Leu Ile Leu Ile Ala Ser
65                  70                  75                  80

Gln Asn His Leu Lys Lys Asp Asn Asn Val Leu Gln Lys Leu Tyr Ile
                85                  90                  95

Ser Ile Leu Ile Ser Leu Gln Ile Leu Leu Ile Ile Thr Phe Ser Ala
            100                 105                 110

Thr Glu Leu Ile Ile Phe Tyr Ile Leu Phe Glu Ala Thr Leu Ile Pro
        115                 120                 125

Thr Leu Ile Ile Ile Thr Arg Trp Gly Asn Gln Thr Glu Arg Leu Asn
    130                 135                 140

Ala Gly Ile Tyr Phe Leu Phe Tyr Thr Leu Ile Gly Ser Ile Pro Leu
145                 150                 155                 160

Leu Ile Ala Leu Ile Leu Ile Gln Asn His Val Gly Thr Leu Asn Leu
                165                 170                 175

Ile Ile Leu Ser Phe Thr Thr His Thr Leu Asp Ala Ser Trp Ser Asn
            180                 185                 190

Asn Leu Leu Trp Leu Ala Cys Ile Ile Ala Phe Leu Ile Lys Ile Pro
        195                 200                 205

Leu Tyr Gly Val His Leu Trp Leu Pro Lys Ala His Val Glu Ala Pro
    210                 215                 220

Ile Ala Gly Ser Ile Ile Leu Ala Ala Ile Leu Leu Lys Leu Gly Ser
225                 230                 235                 240
```

```
Tyr Gly Ile Ile Arg Ile Ser Ile Ile Leu Asp Pro Leu Thr Lys Tyr
            245                 250                 255

Ile Ala Tyr Pro Phe Ile Leu Leu Ser Leu Trp Gly Ile Ile Ile Thr
            260                 265                 270

Ser Ser Ile Cys Leu Arg Gln Thr Asp Leu Lys Ser Leu Ile Ala Tyr
            275                 280                 285

Ser Ser Val Ser His Ile Ala Leu Val Ile Ala Ser Ile Ile Ile Gln
            290                 295                 300

Thr Pro Trp Ser Phe Ile Gly Ala Thr Ile Leu Ile Ile Ala His Gly
305                 310                 315                 320

Leu Thr Ser Ser Leu Leu Phe Cys Leu Ala Asn Ser Asn Tyr Glu Arg
            325                 330                 335

Ile His Ser Arg Thr Ile Ile Met Ala Arg Gly Leu Gln Met Val Phe
            340                 345                 350

Pro Leu Ile Ala Thr Trp Trp Leu Ile Ala Ser Leu Ala Asn Leu Ala
            355                 360                 365

Leu Pro Pro Ser Ile Asn Leu Ile Gly Glu Leu Phe Ile Thr Ile Ser
            370                 375                 380

Leu Phe Ser Trp Ser Asn Phe Thr Ile Ile Leu Ile Gly Ile Asn Ile
385                 390                 395                 400

Ile Ile Thr Gly Ile Tyr Ser Ile Tyr Ile Ile Ile Thr Thr Gln Arg
            405                 410                 415

Gly Lys Leu Thr Asn His Ile Ile Asn Leu Gln Pro Ser His Thr Arg
            420                 425                 430

Glu Leu Thr Leu Ile Ala Leu His Ile Ile Pro Leu Ile Leu Leu Thr
            435                 440                 445

Thr Asn Pro Lys Leu Ile Thr Gly Leu Thr Ile Asp Tyr Lys Asp Asp
450                 455                 460

Asp Asp Lys Met Val Phe Thr Leu Glu Asp Phe Val Gly Asp Trp Arg
465                 470                 475                 480

Gln Thr Ala Gly Tyr Asn Leu Asp Gln Val Leu Glu Gln Gly Gly Val
            485                 490                 495

Ser Ser Leu Phe Gln Asn Leu Gly Val Ser Val Thr Pro Ile Gln
            500                 505                 510
```

```
<210> SEQ ID NO 13
<211> LENGTH: 27
<212> TYPE: PRT
<213> ORGANISM: Artificial Sequence
<220> FEATURE:
<223> OTHER INFORMATION: KALA peptide

<400> SEQUENCE: 13

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala
            20                  25
```

RECOMBINANT EXPRESSION VECTOR AND LIPID MEMBRANE STRUCTURE HAVING SAID VECTOR ENCAPSULATED THEREIN

CROSS-REFERENCE TO RELATED APPLICATIONS

This application is a U.S. national phase application of International Application No. PCT/JP2016/085098, filed Nov. 28, 2016 claiming the benefit of Japanese Application No. 2015-230498, filed Nov. 26, 2015, the contents of each of which are incorporated herein by their entireties for all purposes.

SEQUENCE LISTING

The Sequence Listing for this application is labeled as "SequenceListing.txt", which was created on Jul. 11, 2018, and is 90,593 bytes in size. The entire content of the sequence listing is incorporated herein by reference in its entirety.

TECHNICAL FIELD

The present invention relates to a recombinant expression vector for expressing a target protein in mitochondria in an animal cell, and a lipid membrane structure encapsulating the vector.

BACKGROUND ART

Mitochondrion, one of cellular organelles, has a genomic DNA independent of a cell nucleus. There have been many reports on relationships between mutations in mitochondrial genomic DNA and various diseases (encephalomyopathy, neurodegenerative disease, cancer, diabetes, etc.), and these diseases are generically called mitochondrial diseases.

Methods for treating mitochondrial diseases include a gene therapy for the purpose of expressing in mitochondria a protein that is expected to have a therapeutic effect. As methods for achieving such a therapy, a method for transferring a target protein expressed in cell nuclei into mitochondria and a method using a transgene expression system enabling the direct expression of a target protein in mitochondria are proposed.

In connection with the method for transferring a target protein expressed in cell nuclei into mitochondria, a wide variety of expression vectors have been developed. Many of them utilize a mitochondrial targeting signal peptide (MTS), which mitochondrial proteins encoded by the cell nuclear genome have. In the method utilizing MTS, specifically, an expression vector encoding a target protein having an MTS on the upstream side (MTS-added protein) is delivered to cell nuclei, the MTS-added protein is expressed in cytoplasm and delivered to mitochondria.

This method may be useful for certain target proteins. However, the applicability of this method to mitochondrial proteins encoded by a mitochondrial genomic DNA (mitochondrial endogenous protein), which is expected to be used in gene therapies, is unfortunately low. This is because many mitochondrial endogenous proteins are insoluble in cytoplasm, so that mitochondrial endogenous proteins expressed in cytoplasm will aggregate, resulting in insufficient transfer to mitochondria.

Patent Literature 1 discloses a method for suppressing aggregation of a target protein in cytoplasm using an expression vector encoding an MTS-added protein composed of an MTS having increased solubility and a certain mitochondrial endogenous protein. However, because mitochondrial endogenous proteins often exhibit cytotoxicity in intracellular organelles other than mitochondria, the range of target proteins to which the method disclosed in Patent Literature 1 is applicable is limited.

In addition, the above method using an MTS-added protein may cause lethal damages on cells due to interference or competition with the original intracellular transport of mitochondrial endogenous proteins, and thus there remains a concern in using the method as a tool for gene therapy.

On the other hand, in case of using a transgene expression system enabling the direct expression of a target protein in mitochondria, first, a necessary and sufficient level in the transcription and expression of a target protein in mitochondria is required. To suit such a purpose, several expression vectors have been designed in which a promoter derived from a gene in a mitochondrial genomic DNA, for example, an HSP (heavy strand promoter) is selected, and a DNA encoding a target protein is located under control of the promoter. These expression vector is also devised to have triplet codons frequently used in a mitochondrial genomic DNA. However, the expression level of these expression vectors has not reached a necessary and sufficient level for treating diseases so far.

For example, Non-Patent Literature 1 proposes a method for expressing a target protein by encapsulating a DNA of which transcription is induced in mitochondria under the HSP control into an artificial viral vector onto which an MTS has been added, and introducing the viral vector directly into mitochondria. This method has an advantage that the expression level of the target protein from the introduced viral vector is relatively high. However, the method is accompanied by a problem of viral vector in safety. In addition, it is not completely verified whether the target protein is expressed in mitochondria as desired.

CITATION LIST

Non-Patent Literatures

Non-Patent Literature 1: Yu, H. et al., Proc. Natl. Acad. Sci. USA, 2012, 109, E1238-47.

CITATION LIST

Patent Literatures

Patent Literature 1: US 2015/0225740

SUMMARY OF INVENTION

Technical Problem

An object of the present invention is to provide a novel expression vector capable of efficiently expressing a target protein in mitochondria while suppressing undesired expression of the target protein in cell organelles other than mitochondria.

Solution to Problem

The present inventors have surprisingly confirmed that a promoter having a transcriptional activity in cell nuclei exhibits rather higher transcriptional activity also in mitochondria than a promoter derived from a gene present in a mitochondrial genomic DNA, and found that, by devising to suppress undesired expression of a target protein in cell nuclei, the target protein can be expressed safely in mitochondria, and thus have completed the following inventions.

(1) A recombinant expression vector for expressing a target protein in mitochondria in an animal cell, including a promoter sequence exhibiting a transcriptional activity in a cell nucleus in an animal cell, and a coding region encoding the target protein under control of the promoter sequence, wherein the coding region contains one or more TGAs as a codon corresponding to tryptophan.

(2) The recombinant expression vector according to (1), further including a coding region of a mitochondrial genomic DNA at the 5' terminal side of the coding region encoding the target protein.

(3) The recombinant expression vector according to (1) or (2), including a base sequence corresponding to a mitochondrial tRNA at the 3' terminal side of the coding region encoding the target protein.

(4) The recombinant expression vector according to any one of (1) to (3), wherein the promoter sequence is a base sequence of a promoter selected from the group consisting of Cytomegalovirus promoter, Simian virus 40 promoter, Rous Sarcoma virus promoter, EF1α promoter, β-actin promoter and T7 promoter.

(5) The recombinant expression vector according to (4), wherein the promoter sequence is a base sequence of Cytomegalovirus promoter or Rous Sarcoma virus promoter.

(6) The recombinant expression vector according to any one of (1) to (5), wherein all codons corresponding to tryptophan in the coding region encoding the target protein are TGA.

(7) The recombinant expression vector according to any one of (2) to (6), wherein the coding region of the mitochondrial genomic DNA is a coding region of NADH dehydrogenase, subunit 4.

(8) A lipid membrane structure encapsulating the expression vector according to any one of (1) to (7).

(9) The lipid membrane structure according to (8), containing sphingomyelin as a constitutive lipid of a lipid membrane.

(10) The lipid membrane structure according to (8) or (9), having a peptide consisting of the amino acid sequence represented by SEQ ID NO: 13 on a surface of a lipid membrane.

(11) A lipid membrane structure for introducing a nucleic acid into mitochondria in an animal cell, containing dioleyl phosphatidylethanolamine and sphingomyelin as a constitutive lipid of a lipid membrane, and having a peptide consisting of the amino acid sequence represented by SEQ ID NO: 13 on a surface of the lipid membrane.

Advantageous Effects of Invention

According to the expression vector and the lipid membrane structure of the present invention, it is possible to express a target protein more efficiently and selectively in mitochondria. The expression vector and the lipid membrane structure of the present invention can be used as a medicament superior in safety and efficacy for treating mitochondrial diseases.

DESCRIPTION OF EMBODIMENTS

Figure 1:
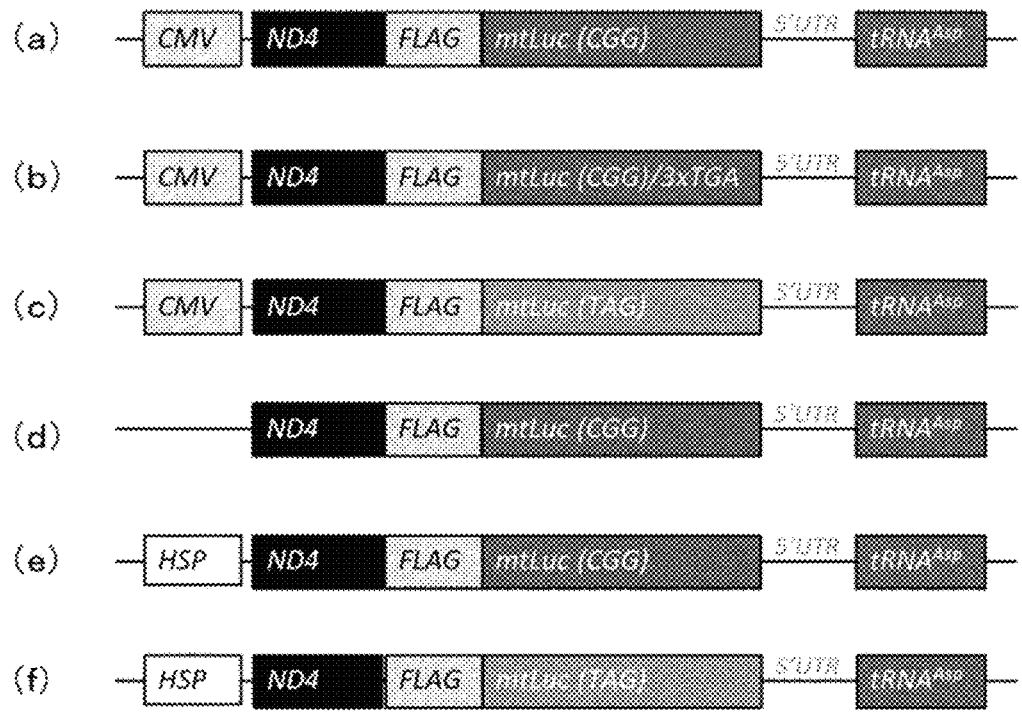
FIG. 1 is a diagram schematically showing the structures of recombinant genes in the expression vectors of the present invention and the expression vectors for comparison.

A first aspect of the present invention relates to a recombinant expression vector for expressing a target protein in mitochondria in an animal cell, including a promoter sequence exhibiting a transcriptional activity in a cell nucleus in an animal cell, and a coding region coding the target protein under control of the promoter sequence, wherein the coding region contains one or more TGAs as a codon corresponding to tryptophan (Trp). In other words, the present invention relates to a recombinant expression vector having the above-described structure, and a specific application of the vector for expressing a target protein in mitochondria in an animal cell.

The promoter sequence usable in the expression vector of the present invention is not particularly limited, as long as it exhibits a transcriptional activity, that is, an ability to induce transcription of mRNA in a cell nucleus of a mammal.

Examples thereof include base sequences of Cytomegalovirus (CMV) promoter, Simian virus (SV) 40 promoter, Rous Sarcoma virus (RSV) promoter, EF1α promoter, β-actin promoter, T7 promoter and the like. CMV promoter or RSV promoter is preferably used. In addition, these promoter sequences may be mutated, such as substituted and others, as long as their transcriptional activities are not impaired.

The target protein in the present invention may be any protein that is desired to be expressed in mitochondria, in other words, to exhibit its function in mitochondria. Examples thereof include, in addition to proteins expected to be effective for treating mitochondrial diseases, proteins whose expression in mitochondria attract an academic interest. From such a viewpoint, the target protein may be any protein, including a protein encoded by a cell nuclear genomic DNA, a mitochondrial protein encoded by a mitochondrial genomic DNA, and a heterologous protein to a cell to be transfected with the vector of the present invention. In addition, there is no particular limitation on the size (number of amino acid residues) or chemical properties (hydrophobicity, hydrophilicity, charge, and other properties) of the protein.

In the present invention, the coding region means a base sequence of a DNA having a start codon and a stop codon at each end, and serving as a template for an mRNA to be translated into a target protein. In this case, the coding region may be composed of a single open reading frame (ORF), or a plurality of exons split by introns. In other words, the coding region may be a base sequence of a DNA which can be induced to be transcribed by the promoter sequence, and can provide an mRNA to be finally translated into a target protein in mitochondria as described below.

For the expression vector of the present invention, a coding region containing one or more TGAs as a codon corresponding to Trp is used. Preferably, a coding region in a mitochondrial genomic DNA, a coding region in which TGG (UGG on an mRNA) is artificially changed into TGA which is a codon corresponding to Trp, a coding region in which a codon at a position where the activity of a target protein can be retained even when the amino acid residue is replaced with a Trp residue is artificially changed into TGA, and the like are used. Such an artificial change of codon can be carried out using a general gene recombination technology.

TGA corresponds to a stop codon in an mRNA translated in cytoplasm, while TGA corresponds to a codon encoding Trp in an mRNA translated in mitochondria. Therefore, when an animal cell is transformed with the expression vector of the present invention, even in case where the expression vector reaches the cell nucleus and an mRNA is transcribed from the coding region, synthesis of a target protein encoded in the coding region arrests at a position of TGA. As a result, the target protein is not synthesized, at least wholly. This makes it possible to suppress the negative influence due to synthesis of the whole target protein in cytoplasm.

On the other hand, when the expression vector of the present invention reaches a mitochondrion and an mRNA is transcribed from the coding region, synthesis of a target protein encoded in the coding region proceeds without arresting at a position of TGA. As a result, the whole target protein is synthesized appropriately, and can exhibit its function in the mitochondrion.

From the viewpoint of suppressing undesired expression of a target protein in cytoplasm, in the present invention, it is preferable to use a coding region containing a plurality of TGAs. In addition, from the viewpoint of more reliably suppressing undesired expression of a function of a target protein in cytoplasm, it is more preferable to use a coding region containing one or more TGAs at a position closer to the 5' terminal (N terminal of a target protein). Furthermore, when a target protein is a protein that is translated normally in cytoplasm, it is preferable to appropriately modify a coding sequence so as to use mitochondrial codons for codons other than above-described TGA. One example of the above is to modify AGG, which encodes an Arg residue in a cell nuclear genome, while encoding a stop codon in a mitochondrial genome, into CGG, which encodes an Arg residue in either a cell nuclear genome or a mitochondrial genome.

Having a coding region under control of a promoter sequence means that the coding region is transcriptionally linked to the promoter sequence, that is, the coding region is present within a range where transcription to an mRNA is initiated by the transcriptional activity of the promoter sequence. Examples thereof includes a case where a start codon for the coding region is present within a range of about 1 to bases from the 3' terminal of the promoter sequence, but such a range varies depending on the type of promoter sequence, and may be appropriately adjusted by a person skilled in the art.

The expression vector of the present invention preferably further includes a coding region of a mitochondrial genomic DNA at the 5' terminal side of a coding region encoding a target protein. In particular, a coding region of a mitochondrial genomic DNA and a coding region encoding a target protein are preferably linked to each other in-frame, that is, linked so as to synthesize a fusion protein consisting of a consecutive amino acid sequence of an amino acid sequence encoded by a coding region of a mitochondrial genomic DNA and an amino acid sequence of a target protein. It may be inferred that a protein molecule transcribed and translated from a recombinant gene of the expression vector would be stabilized in mitochondria when the protein molecule contains in its part a protein molecule endogenously transcribed and translated and exhibiting its function stably in mitochondria.

It is known that 13 kinds of coding regions are present in a mitochondrial genomic DNA, and any of the coding regions can be used in the present invention. Among them, it is particularly preferable to use a coding region corresponding to an ND4 (NADH dehydrogenase, subunit 4) protein, particularly a human ND4 protein.

The expression vector of the present invention preferably includes, at the 3' terminal side of a coding region, a base sequence corresponding to a mitochondrial tRNA, particularly a base sequence corresponding to the tRNA together with a base sequence containing the 5' terminal untranslated region of the base sequence corresponding to the tRNA. The type of mitochondrial tRNA to be selected is not particularly limited. It may be inferred that an RNA molecule transcribed from a recombinant gene of the expression vector would be stabilized in mitochondria when the RNA molecule contains in its part a base sequence of an RNA molecule endogenously transcribed and exhibiting its function stably in mitochondria.

A second aspect of the present invention provides a lipid membrane structure for introducing a nucleic acid into mitochondria in an animal cell, and a lipid membrane structure encapsulating the above-described expression vector. The lipid membrane structure of the present invention includes, as a constitutive lipid of the lipid membrane, sphingomyelin (SM), preferably dioleyl phosphatidylethanolamine (DOPE) and SM. The lipid membrane structure of the present invention also preferably includes a peptide consisting of the amino acid sequence represented by SEQ ID NO: 13 (hereinafter referred to as KALA peptide) on the surface of the lipid membrane. A preferred specific example of the lipid membrane structure is a lipid membrane structure disclosed in detail, along with its preparation method, in Patent Literature 2 (JP 5067733 B), in which DOPE and SM are contained as constitutive lipids of the lipid membrane, and the surface of the lipid membrane is modified with KALA peptide. Patent Literature 2 is incorporated herein by reference in its entirety.

KALA peptide is disclosed in Shaheen et al. (Biomaterials, 2011, 32, 6342-6350), as a lipid membrane fusogenic peptide having a function of promoting membrane fusion between lipid membranes. The present invention utilizes the deliverability of KALA peptide to mitochondria, based on the finding that KALA peptide placed on the surface of the lipid membrane structure exhibits the ability to selectively deliver the lipid membrane structure to mitochondria of intracellular organelles.

A lipid membrane structure in which the expression vector of the present invention is encapsulated, DOPE and SM are contained as constitutive lipids of the lipid membrane, and KALA peptide is present on the surface of the lipid membrane is the most preferable in the present invention, and such lipid membrane structure may be produced by, in accordance with a method for preparing stearylated octaarginine (STR-R8) and a method for producing a lipid membrane structure that is modified with octaarginine and encapsulates a DNA, as disclosed in Patent Literature 2, replacing the octaarginine and the DNA with KALA peptide and the expression vector of the present invention, respectively.

Both of the expression vector and the lipid membrane structure encapsulating the same of the present invention can be used as a medicament for use in treatment of mitochondrial diseases. A third aspect of the present invention relates to such a medicament, and a method for treating mitochondrial diseases including administering an effective amount of such a medicament to a patient. The medicament of the present invention can be used as a nucleic acid medicament or liposomal medicament or preparation in accordance with a generally known dosage form, dosage, administration and the like.

For example, the medicament of the present invention can be used in the form of parenteral formulations such as injections and drips. In addition, examples of carriers that can be used in such parenteral formulations include aqueous carriers such as physiological saline and isotonic solution containing glucose, D-sorbitol and the like.

The medicament of the present invention may further be in the form of a composition containing components such as a pharmaceutically acceptable buffer, stabilizer, preservative and other additives. Such pharmaceutically acceptable components are well known to a person skilled in the art. A person skilled in the art can select and use the pharmaceutically acceptable components, for example from those described in Japanese Pharmacopoeia, Sixteenth Edition or other standards, within the scope of his/her normal implementation ability, depending on dosage forms.

A method for administering the medicament of the present invention is not particularly limited. When the medicament is a parenteral formulation, intravascular administration (preferably intravenous administration), intraperitoneal administration, intestinal administration, subcutaneous administration and the like can be recited. In one preferable embodiment, the therapeutic agent of the present invention is administered to a living body via intravenous administration.

Detailed description of the present invention will be further made with reference to the following Examples and Experimental Examples. In the Examples and Experimental Examples, luciferase is used as a model of a target protein.

Example 1

1) Construction of Expression Vector

The following vectors of a) to f) were constructed using a general gene recombination technology.

a) pCMV-mtLuc(CGG)

This vector is an expression vector of the present invention, in which a recombinant gene including, in the following order, a CMV promoter sequence, a coding region of a mitochondrial genomic DNA encoding a mitochondrial protein ND4 (ND4), a base sequence encoding a FLAG tag (FLAG), a coding region encoding a codon-modified luciferase whose codons encoding the 479th Trp residue and the 512th Arg residue in the amino acid residues represented by SEQ ID NO: 1 are TGA and CGG respectively (mtLuc), and a base sequence encoding a mitochondrial tRNA$^{Asp}$ with its 5' terminal untranslated region (FIG. 1(a), SEQ ID NO: 1) is incorporated into a pBluescript SK(-) vector (Stratagene) whose ring is opened with EcoRI and SmaI. Note that the codon TGA encoding the 479th Trp residue and the codon CGG encoding the 512th Arg residue are TGG and AGG in the wild-type luciferase, respectively. In addition, the amino acid sequence represented by SEQ ID NO: 1 and SEQ ID NO: 2 is the amino acid sequence into which the base sequence of SEQ ID NO: 1 is translated using codons employed in mitochondria.

Because the recombinant gene has one TGA codon in the coding region encoding luciferase, active luciferase is expressed in mitochondria but not expressed (not translated) in cell nuclei.

b) pCMV-mtLuc(CGG)/3×TGA

This vector is an expression vector of the present invention that has the same structure as pCMV-mtLuc(CGG) in a), except that codons encoding the 601th and 630th Trp residues shown in SEQ ID NO: 1 are TGAs (FIG. 1(b), SEQ ID NO: 3). Note that the TGA codons encoding the 601th and 630th Trp residues are both TGGs in the wild-type luciferase. In addition, the amino acid sequence represented by SEQ ID NO: 3 and SEQ ID NO: 4 is the amino acid sequence into which the base sequence of SEQ ID NO: 3 is translated using codons employed in mitochondria.

Because the vector has three TGA codons in the coding region encoding luciferase, active luciferase is expressed in mitochondria but not expressed (not translated) in cell nuclei.

c) pCMV-mtLuc(TAG)

This vector is a vector that has the same structure as pCMV-mtLuc(CGG) in a), except that the 512th codon shown in SEQ ID NO: 1 is TAG (FIG. 1(c), SEQ ID NO: 5). Note that the 512th codon is AGG in the wild-type luciferase. In addition, the amino acid sequence represented by SEQ ID NO: 5 and SEQ ID NO: 6 is the amino acid sequence into which the base sequence of SEQ ID NO: 5 is translated using codons employed in mitochondria.

This vector is a translation-negative control vector with which active luciferase is not expressed (translated) in either cell nuclei or mitochondria because TAG serves as a stop codon both in the cell nucleus and the mitochondria.

d) pmtLuc

This vector is a vector in which the CMV promoter sequence is deleted from the recombinant gene of pCMV-mtLuc(CGG) in a) (FIG. 1(d), SEQ ID NO: 7). Because this vector does not have a promoter sequence, it is a transcription-negative control vector with which the recombinant gene is not transcribed in either cell nuclei or mitochondria. The amino acid sequence represented by SEQ ID NO: 7 and SEQ ID NO: 8 is the amino acid sequence into which the base sequence of SEQ ID NO: 7 is translated using codons employed in mitochondria.

e) pHSP-mtLuc(CGG)

This vector is a comparative vector in which the CMV promoter sequence in the recombinant gene of pCMV-mtLuc(CGG) in a) is replaced with HSP (FIG. 1(e), SEQ ID NO: 9). The amino acid sequence represented by SEQ ID NO: 9 and SEQ ID NO: 10 is the amino acid sequences into which the base sequence of SEQ ID NO: 9 is translated using codons employed in mitochondria.

f) pHSP-mtLuc(TAG)

This vector is a comparative translation-negative control vector in which the CMV promoter sequence in the recombinant gene of pCMV-mtLuc(TAG) in c) is replaced with HSP (FIG. 1(f), SEQ ID NO: 11). The amino acid sequence represented by SEQ ID NO: 11 and SEQ ID NO: 12 is the amino acid sequence into which the base sequence of SEQ ID NO: 11 is translated using codons employed in mitochondria.

2) Introduction of Vectors into Cell and Confirmation of their Expression

Figure 2:
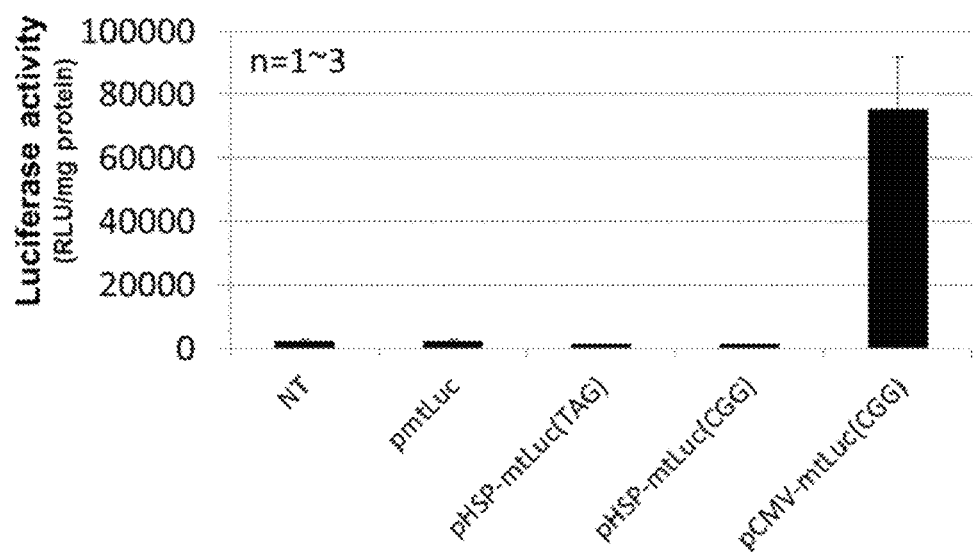
FIG. 2 is a graph showing the expression levels (emission intensities) of the target protein (luciferase) in the liver of mice to which the expression vector of the present invention and the expression vectors for comparison are administered respectively by a hydrodynamics method.

Two mL of vector solution containing one of the four vectors, pCMV-mtLuc(CGG), pHSP-mtLuc(CGG), pHSP-mtLuc(TAG) and pmtLuc (100 μg/5% glucose solution) were administered into the tail vein of C57BL/6N mice (6 weeks old, male) using a 27 G needle for 5 seconds, with reference to the hydrodynamics method disclosed in Yasu-zaki et al. (J Control Release, 2013, 172(3): 805-11). The livers were collected 6 hours after administration, and the emission levels of luciferase were measured using a Luciferase assay reagent (Promega) in accordance with the manufacturer's protocol. The results are shown in FIG. 2.

It was confirmed that pCMV-mtLuc(CGG) led to the markedly higher emission level of luciferase compared to the comparative vector pHSP-mtLuc(CGG) and thus had the higher gene expression efficiency.

Figure 3:
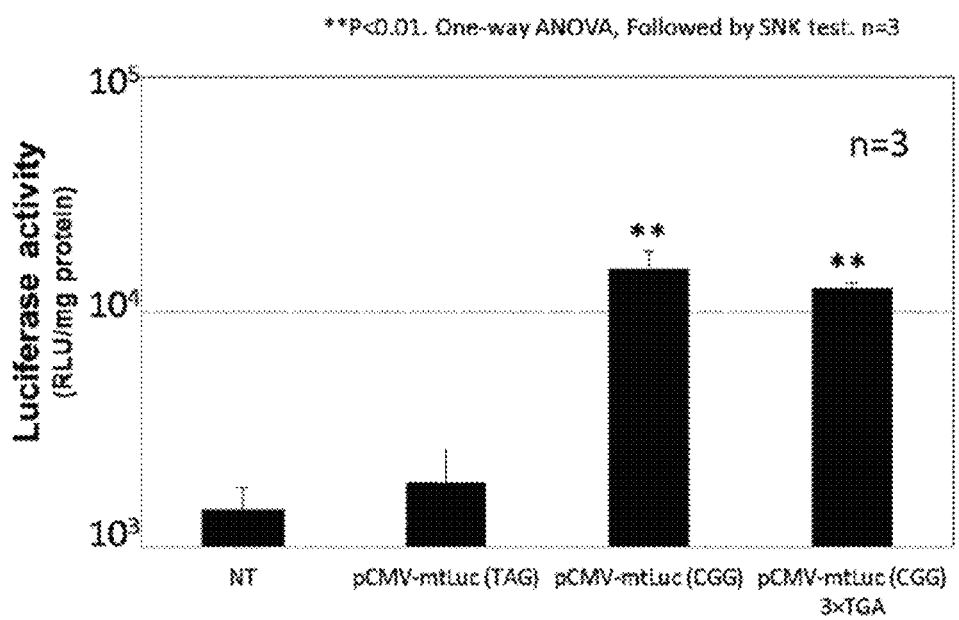
FIG. 3 is a graph showing the expression levels (emission intensities) of the target protein (luciferase) in the liver of mice to which the expression vectors of the present invention and the expression vector for comparison are administered respectively by a hydrodynamics method.

In addition, similar experiments were performed on pCMV-mtLuc(CGG), pCMV-mtLuc(CGG)3×TGA and pCMV-mtLuc(TAG), and it was confirmed that the gene expression efficiency of pCMV-mtLuc(CGG)3×TGA was equivalent to that of pCMV-mtLuc(CGG) (FIG. 3).

Example 2 Introduction into HeLa Cell

In a 24-well plate, 4×10$^4$ HeLa cells (0.5 mL) were seeded, and after 24 hours, a DMEM solution of Lipofectamine (0.25 mL, without serum or antibiotic) containing 0.4 μg or 1 μg of pCMV-mtLuc(CGG) or pmtLuc(CGG) was added to the cells, followed by incubation for 3 hours under 5% CO$_2$. Then, the medium was replaced with a fresh medium containing 10% serum, followed by the additional incubation for 21 hours.

The cells were washed with 0.5 mL of PBS and then lysed with 75 μL of a reporter lysis buffer (Promega). After incubation at −80° C. for 30 minutes or more, thawing was carried out for approximately 10 to 15 minutes at room temperature. Thereafter, the cells were collected from the plate and transferred into an Eppendorf tube, followed by centrifugation at 15,000 g, 4° C. for 5 minutes to collect 50 μL of the supernatant. 50 μL of a NanoLuc assay reagent (Promega) were added to 20 μL of the cell lysates, and the luciferase activities were measured using a luminometer. The protein contents in the cell lysates were determined using a BCA protein assay kit (PIERCE), with which the luciferase activities were corrected. The results are shown in FIG. 4.

Figure 4:
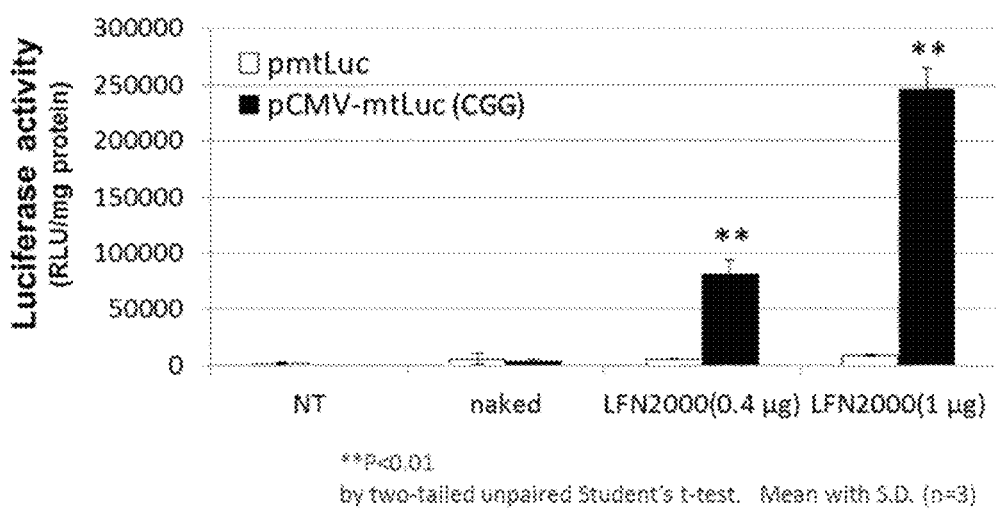
FIG. 4 is a graph showing the expression levels (emission intensities) of the target protein (luciferase) in HeLa cells transfected with the expression vector of the present invention and the expression vector for comparison.

It was confirmed that the emission intensities of luciferase resulting from the transfection of pCMV-mtLuc(CGG) were enhanced with an increase of the added amount (FIG. 4). On the other hand, the luciferase emissions were not observed for the cells to which transcription-negative control pmtLuc was added or the cells to which the vectors were added without using Lipofectamine 2000 (naked).

Example 3 Construction of Lipid Membrane Structure

1) In accordance with the method disclosed in Patent Literature 2, by using KALA peptide, a membrane fusogenic peptide (Shaheen et al., Biomaterials, 2011, 32, 6342-6350, SEQ ID NO: 13) instead of octaarginine in stearylated octaarginine (STR-R8), a conjugate of KALA and stearic acid (STR-KALA) was prepared.

2) In a test tube, 825 μL of 1 mM lipid solution (1,2-dioleyl sn-glycero-3-phosphoethanolamine (DOPE)/SM/CHEMS=9/2/1) and 720 μL of chloroform were added and mixed, followed by drying in vacuum to produce a lipid membrane film. To this film, 1.5 mL of 10 mM HEPES buffer were added, and the resultant was hydrated for 15 minutes at room temperature. Subsequently, ultrasonic treatment was carried out with a bath-type sonicator (AU-25C; Aiwa Ika Kohgyo) for 30 seconds and with a probe-type sonicator for 10 minutes to prepare a small unilamellar vesicles (SUV) solution.

By adding dropwise 0.1 mg/mL of pCMV-mtLuc(CGG) solution to 0.1 mg/mL of protamine solution, nucleic acid nanoparticles were prepared (nitrogen/phosphate (N/P) ratio of 3.0). The nanoparticles were mixed with the SUV solution in 2) at a volume ratio of 1:2. To the mixture, STR-KALA in 1) was further added (in the amount corresponding to 10 mol % of the total lipid) to prepare a lipid membrane structure having KALA peptide on its surface (KALA-MITO-Porter(SM)).

For comparison, STR-KALA in KALA-MITO-Porter(SM) was replaced with STR-R8 to prepare R8-MITO-Porter(SM), SM in KALA-MITO-Porter(SM) was replaced with an equal amount of phosphatidic acid (PA) to prepare KALA-MITO-Porter(PA), and STR-KALA in KALA-MITO-Porter(PA) was replaced with STR-R8 to prepare R8-MITO-Porter(PA), respectively.

Figure 5:
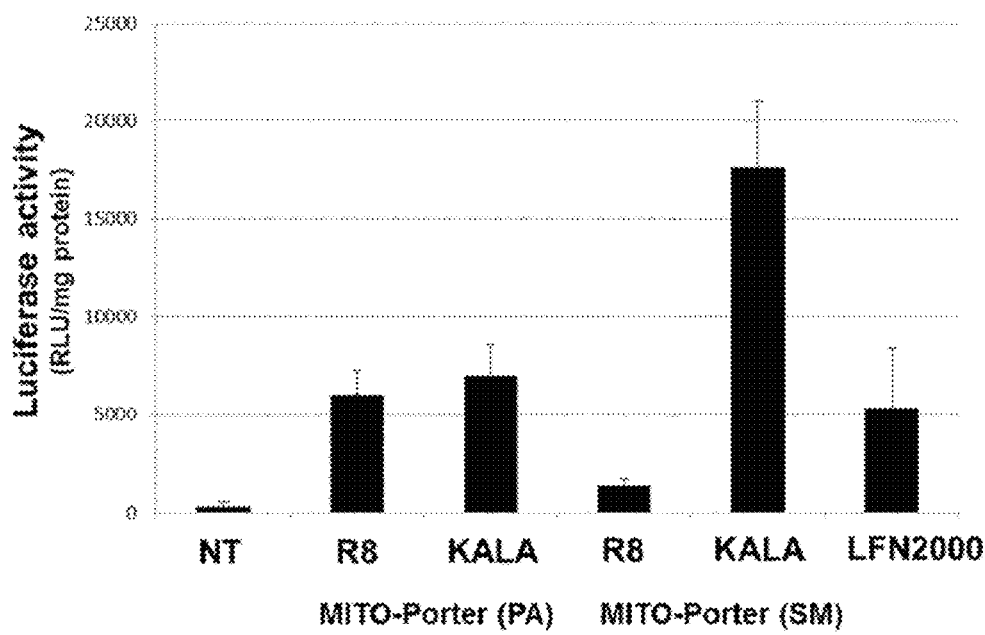
FIG. 5 is a graph showing the expression levels (emission intensities) of the target protein (luciferase) in HeLa cells transfected with the lipid membrane structures of the present invention encapsulating the expression vector of the present invention and the lipid membrane structures for comparison.

In the same manner as in Example 2, HeLa cells (8×10$^4$ cells, 0.5 mL) were transfected with each of the lipid membrane structures, and the luciferase emissions were measured. The results are shown in FIG. 5. Compared with Lipofectamine 2000, the emission intensity of luciferase caused by KALA-MITO-Porter(SM) encapsulating pCMV-mtLuc(CGG) was greatly enhanced, while the emission intensity of luciferase caused by R8-MITO-Porter(SM) was hardly observed. In addition, the emission intensity of luciferase caused by either R8-MITO-Porter(PA) or KALA-MITO-Porter(PA) was not substantially different from that caused by Lipofectamine 2000.

The following Experimental Examples are experiments for confirming that the luciferase emission resulting from the transfection with the expression vector of the present invention is not through transcription and translation in cell nuclei.

Experimental Example 1 Experiment for In Vitro Translation

By using a HeLa Scribe Nuclear Extract in vitro Transcription System (Promega), a wild-type luciferase-mRNA was prepared from a plasmid pNL1.1 [CMV/nLuc] (Promega) in which a gene encoding wild-type luciferase was ligated to the downstream of the CMV promoter sequence. Furthermore, in the same manner, an mtLuc(CGG)-mRNA and mtLuc(TAG)-mRNA were prepared from pCMV-mtLuc(CGG) and pCMV-mtLuc(TAG).

Figure 6:
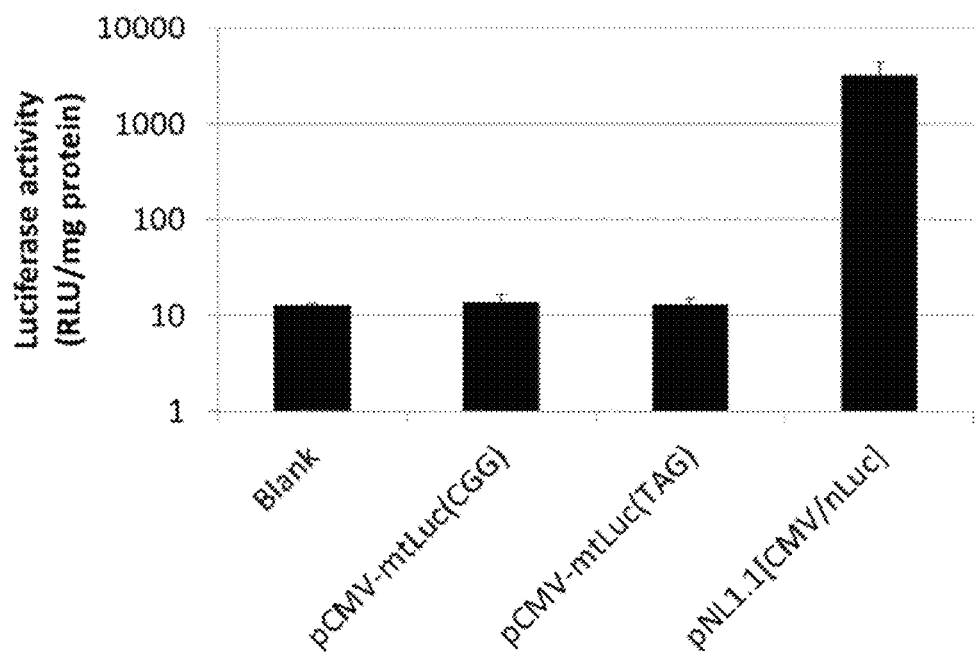
FIG. 6 is a graph showing the expression levels (emission intensities) of the target protein (luciferase) into which mRNAs transcribed from the expression vector of the present invention and the expression vectors for comparison are translated using an in vitro translation system utilizing rabbit reticulocytes.

By using an in vitro translation system utilizing rabbit reticulocytes (Promega), each of the above-described mRNAs was translated and proteins were synthesized, and the luciferase emissions were measured. The results are shown in FIG. 6.

Mitochondria do not exist in rabbit reticulocytes. Accordingly, it is expected that luciferase would be synthesized from the wild type NLuc-mRNA, but would not be synthesized from the mtLuc(CGG)-mRNA because it has a stop codon TGA, and active luciferase would not be synthesized from the mtLuc(TAG)-mRNA either because it has a stop codon TAG. As expected, the luciferase emission was observed for the pNL1.1 [CMV/nLuc] having the wild type NLuc, but the luciferase emission was not observed either for pCMV-mtLuc(CGG) having mtLuc(CGG) or pCMV-mtLuc(TAG) having mtLuc(TAG).

Experimental Example 2 Experiment for Addition of α-Amanitin

Figure 7:
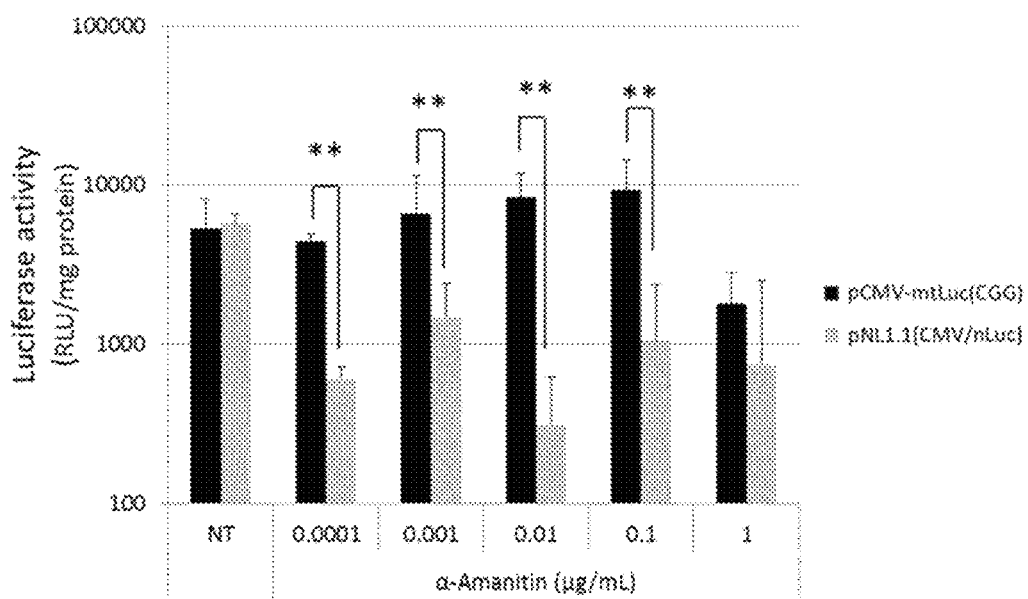
FIG. 7 is a graph showing the expression levels (emission intensities) of the target protein (luciferase) in the presence of α-amanitin having an activity of inhibiting transcription in cell nuclei in HeLa cells transfected with the expression vector of the present invention and the expression vector for comparison.

In a 24-well plate, 4×10$^4$ HeLa cells (0.5 mL) were seeded and incubated for 24 hours in the presence of 0.0001 to 1 μg/mL α-amanitin. Thereafter, in the same manner as the procedure in Example 2, the cells were transfected with pCMV-mtLuc(CGG) or pNL1.1 [CMV/nLuc], and the emission intensities of luciferase were measured. The results are shown in FIG. 7.

α-amanitin inhibits transcription within cell nuclei, therefore, it is expected that the transcription of the pNL1.1 [CMV/nLuc] encoding the mRNA which is produced through transcription within cell nuclei would be inhibited and thus the luciferase activity therefrom would decrease. As expected, the emission intensity of luciferase in the presence of α-amanitin in the HeLa cells transfected with the pNL1.1 [CMV/nLuc] markedly decreased compared to that of the control to which α-amanitin was not added. On the other hand, it is expected that the luciferase activity from pCMV-mtLuc(CGG) would be maintained regardless of the presence or absence of α-amanitin because pCMV-mtLuc(CGG) transcribes mRNA in mitochondria. As expected, α-amanitin in an added amount of 0.0001 to 0.1 μg/mL at which cytotoxicity is not observed did not lower the emission intensity of luciferase in the HeLa cells transfected with pCMV-mtLuc(CGG).

Example 4 Change of Promoter Sequence

The CMV promoter sequences in pCMV-mtLuc(CGG) in 1)a) of Example 1 were replaced with the RSV promoter sequence incorporated in pRc/RSV (invitrogen), the T7 promoter sequence incorporated in pBluescript II SK(+) (Stratagene) or the SV40 promoter sequence incorporated in pGL3-Control (Promega) to construct expression vectors (pRSV-mtLuc(CGG), pT7-mtLuc(CGG) and pSV40-mtLuc(CGG)), respectively.

Figure 8:
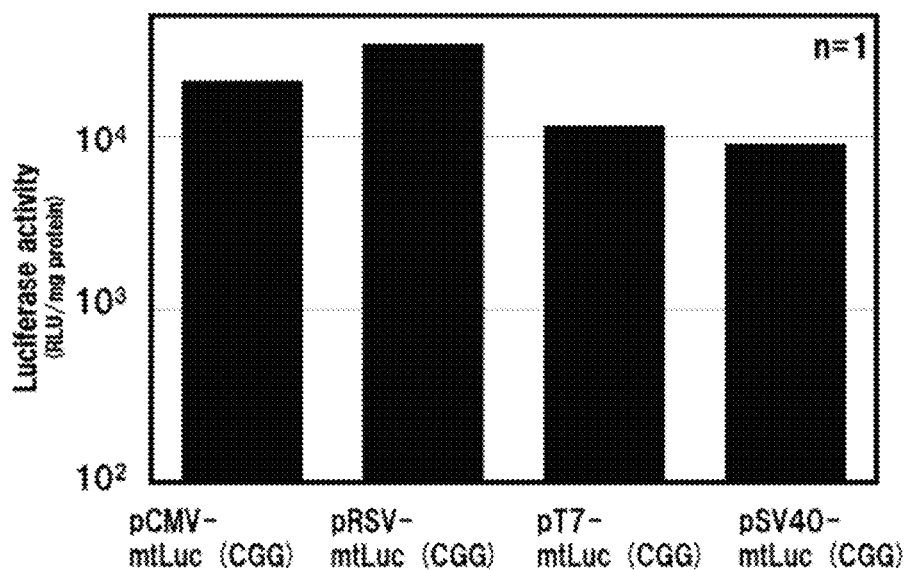
FIG. 8 is a graph showing the expression levels (emission intensities) of the target protein (luciferase) in the liver of mice to which the expression vectors of the present invention having various promoter sequences are administered respectively by a hydrodynamics method.

In the same manner as in 2) of Example 1, 2 mL of vector solution containing one of the four expression vectors, pCMV-mtLuc(CGG), pRSV-mtLuc(CGG), pT7-mtLuc(CGG) and pSV40-mtLuc(CGG) (100 μg/5% glucose solution) were administered into the tail vein of C57BL/6N mice (6 weeks old, male) using a 27 G needle for 5 seconds, with reference to the hydrodynamics method disclosed in Yasuzaki et al. (J Control Release, 2013, 172(3): 805-11). The livers were collected 6 hours after administration, and the emission levels of luciferase were measured using a Luciferase assay reagent (Promega) in accordance with the manufacturer's protocol. The results are shown in FIG. 8.

In all of mice to which the above-described four kinds of expression vectors were administered, the expressions of luciferase in the liver were confirmed. In particular, the highest expression was observed in mice to which pRSV-mtLuc(CGG) was administered.

Example 5 Change of ND4 Sequence

The ND4 sequence and the FLAG sequence in pCMV-mtLuc(CGG) in 1)a) of Example 1 were removed and the mtLuc(CGG) sequence was ligated to the immediate downstream of the CMV promoter sequence to construct an expression vector (pCMV-mtLuc(CGG)[-ND4]). Furthermore, the ND4 sequence in pCMV-mtLuc(CGG) in 1)a) of Example 1) was replaced with a base sequence from position 10,760 to position 12,136 of the base sequence registered as NCBI accession number NC 012920 (Human ND4 sequence) to construct an expression vector (pCMV-mtDNA(human)).

Figure 9:
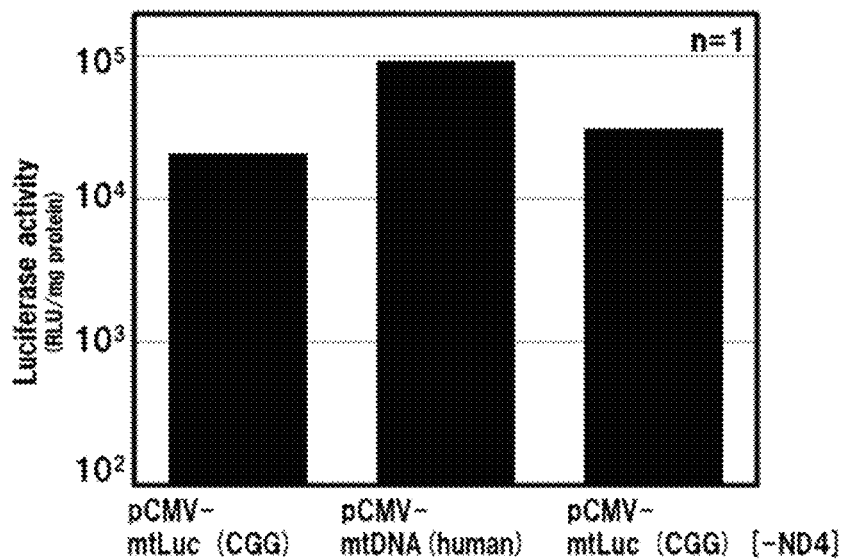
FIG. 9 is a graph showing the expression levels (emission intensities) of the target protein (luciferase) in the liver of mice to which the expression vector of the present invention from which an ND4 sequence is removed or the expression vector of the present invention into which a human ND4 sequence is incorporated are administered respectively by a hydrodynamics method.

In the same manner as in 2) of Example 1, 2 mL of vector solution containing pCMV-mtLuc(CGG), pCMV-mtLuc(CGG)[-ND4] or pCMV-mtDNA(human) (100 μg/5% glucose solution) were administered into the tail vein of C57BL/6N mice (6 weeks old, male) using a 27 G needle for 5 seconds, with reference to the hydrodynamics method disclosed in Yasuzaki et al. (J Control Release, 2013, 172(3): 805-11). The livers were collected 6 hours after administration, and the emission levels of luciferase were measured using a Luciferase assay reagent (Promega) in accordance with the manufacturer's protocol. The results are shown in FIG. 9.

In all of mice to which the above-described three kinds of expression vectors were administered, the expressions of luciferase in the liver were confirmed. In particular, the expression of luciferase observed in mice to which pCMV-mtDNA(human) was administered was higher, compared to that in mice to which pCMV-mtLuc(CGG) was administered.

Example 6 Transformation Using Lipid Structure

Figure 10:
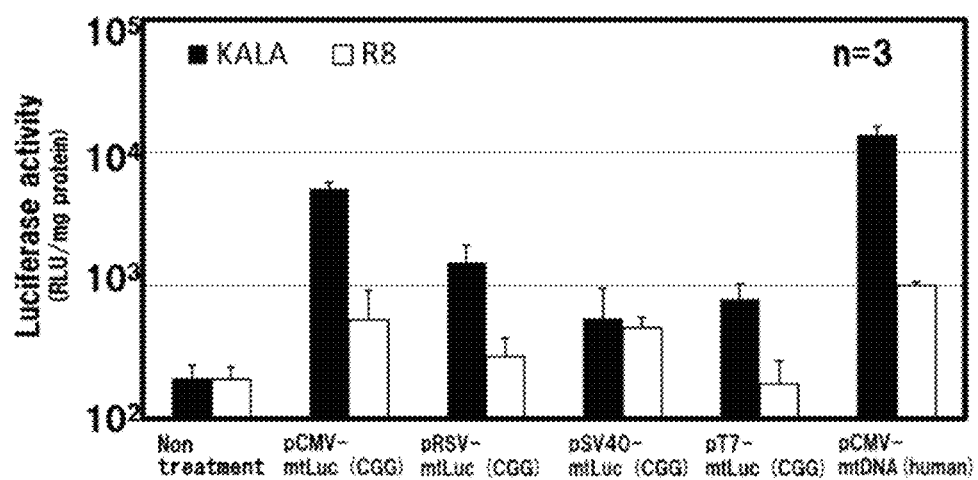
FIG. 10 is a graph showing the expression levels (emission intensities) of the target protein (luciferase) in HeLa cells transfected with the lipid membrane structures of the present invention encapsulating the expression vectors having various promoter sequences.

In accordance with the method described in Example 3, pCMV-mtLuc(CGG) in 1)a) of Example 1, pRSV-mtLuc(CGG), pT7-mtLuc(CGG), SV40-mtLuc(CGG) in Example 4, and pCMV-mtDNA(human) in Example 5 were encapsulated in KALA-MITO-Porter(SM) or R8-MITO-Porter (SM). Then, in the same manner as in Example 2, HeLa cells (8×10$^4$ cells, 0.5 mL) were transfected with each of the lipid membrane structures, and the luciferase emissions were measured. The results are shown in FIG. 10.

For all vectors used, the emission intensities of luciferase observed in cells transfected with vector-encapsulated KALA-MITO-Porters were higher than those observed in cells transfected with vector-encapsulated R8-MITO-Porters. In addition, the highest emission intensity of luciferase was observed in cells transfected with KALA-MITO-Porter encapsulating pCMV-mtDNA(human).

INDUSTRIAL APPLICABILITY

The expression vector and the lipid membrane structure of the present invention both have industrial applicability as a medicament in gene therapy for mitochondrial diseases and as research tools.

The invention claimed is:

1. A recombinant expression vector for expressing a target protein in mitochondria in an animal cell, comprising a promoter exhibiting a transcriptional activity in a cell nucleus in the animal cell and the mitochondria, and a coding region encoding the target protein under control of the promoter, wherein the target protein is a mitochondrial endogenous protein encoded by the coding region in the expression vector, wherein the coding region contains one or more TGAs as a codon corresponding to tryptophan, and wherein the promoter is selected from the group consisting of Cytomegalovirus promoter, Simian virus 40 promoter, Rous Sarcoma virus promoter, EF1α promoter, and β-actin promoter.

2. The recombinant expression vector of claim 1, further comprising a coding region of a mitochondrial genomic DNA at the 5' terminal side of the coding region encoding the target protein.

3. The recombinant expression vector of claim 2, wherein the coding region of the mitochondrial genomic DNA is a coding region of NADH dehydrogenase, subunit 4.

4. The recombinant expression vector of claim 1, further comprising a base sequence corresponding to a mitochondrial tRNA at the 3' terminal side of the coding region encoding the target protein.

5. The recombinant expression vector of claim 1, wherein the promoter is a Cytomegalovirus promoter or Rous Sarcoma virus promoter.

6. The recombinant expression vector of claim 1, wherein all codons corresponding to tryptophan in the coding region encoding the target protein are TGA.

7. A lipid membrane structure encapsulating the recombinant expression vector of claim 1 and a lipid membrane.

8. The lipid membrane structure of claim 7, wherein the lipid membrane comprises sphingomyelin as a constitutive lipid.

9. The lipid membrane structure of claim 7, further comprising a peptide consisting of the amino acid sequence set forth in SEQ ID NO: 13 on a surface of the lipid membrane.

10. The lipid membrane structure of claim 7, wherein the recombinant expression vector further comprises a coding region of a mitochondrial genomic DNA at the 5' terminal side of the coding region encoding the target protein.

11. The lipid membrane structure of claim 10, wherein the coding region of the mitochondrial genomic DNA is a coding region of NADH dehydrogenase, subunit 4.

12. The lipid membrane structure of claim 7, wherein the recombinant expression vector further comprises a base sequence corresponding to a mitochondrial tRNA at the 3' terminal side of the coding region encoding the target protein.

13. The lipid membrane structure of claim 7, wherein the promoter is Cytomegalovirus promoter or Rous Sarcoma virus promoter.

14. The lipid membrane structure of claim 7, wherein all codons corresponding to tryptophan in the coding region encoding the target protein are TGA.

* * * * *